(12) United States Patent
Kraus et al.

(10) Patent No.: US 10,607,737 B2
(45) Date of Patent: Mar. 31, 2020

(54) SYSTEMS AND METHODS TO DERIVE MODELS TO EVALUATE BEHAVIOR OUTCOMES BASED ON BRAIN RESPONSES TO COMPLEX SOUNDS

(71) Applicant: Northwestern University, Evanston, IL (US)

(72) Inventors: Nina Kraus, Evanston, IL (US); Trent Nicol, Libertyville, IL (US); Travis White-Schwoch, Evanston, IL (US)

(73) Assignee: Northwestern University, Evanston, IL (US)

( * ) Notice: Subject to any disclaimer, the term of this patent is extended or adjusted under 35 U.S.C. 154(b) by 603 days.

(21) Appl. No.: 15/001,674

(22) Filed: Jan. 20, 2016

(65) Prior Publication Data

US 2016/0217267 A1 Jul. 28, 2016

Related U.S. Application Data

(60) Provisional application No. 62/105,561, filed on Jan. 20, 2015.

(51) Int. Cl.
*G16H 50/50* (2018.01)
*A61B 5/0484* (2006.01)
(Continued)

(52) U.S. Cl.
CPC ......... *G16H 50/50* (2018.01); *A61B 5/04845* (2013.01); *A61B 5/7267* (2013.01);
(Continued)

(58) Field of Classification Search
CPC ...... G16H 50/50; A61B 5/04845; A61B 5/16; A61B 5/7267; A61B 5/7253; A61B 5/7282; G06F 19/3437; G06K 9/00536
See application file for complete search history.

(56) References Cited

U.S. PATENT DOCUMENTS

2012/0197153 A1    8/2012   Kraus et al.

FOREIGN PATENT DOCUMENTS

| WO | 2006026548 | 3/2006 |
| WO | 2006122304 | 11/2006 |
| WO | 2014138987 | 9/2014 |

OTHER PUBLICATIONS

Travis White-Schwoch et al Physiologic discrimination of stop consonants relates to phonological skills in pre-readers: a biomarker for subsequent reading ability (Year: 2013).*

(Continued)

*Primary Examiner* — Brian W Wathen
*Assistant Examiner* — Abdou K Seye
(74) *Attorney, Agent, or Firm* — Quarles & Brady LLP; Jonathan Stone

(57) ABSTRACT

Disclosed systems and methods analyze a complex auditory response to generate a particular model for a behavioral outcome. An example method includes analyzing one or more response to a complex stimulus to identify regions in each response and peaks in each region. The example method includes constructing a behavioral outcome model based on region and peak information by evaluating a plurality of parameters based on the information associated with the regions and peaks and applying a best fit analysis to include and/or exclude parameters from the plurality of parameters to determine parameters and relationship between the parameters to form the model. The example method includes facilitating application of the model to generate a score by obtaining values for the parameters forming the model and combining the values according to the relationship between the parameters specified in the model, the score indicative of the behavior outcome with respect to at least one first subject.

32 Claims, 15 Drawing Sheets

(51) Int. Cl.
 A61B 5/00 (2006.01)
 G06K 9/00 (2006.01)
(52) U.S. Cl.
 CPC ........... A61B 5/7253 (2013.01); A61B 5/7282 (2013.01); G06K 9/00536 (2013.01)

(56) References Cited

OTHER PUBLICATIONS

Gojko Zaric eta l. "Reduced Neural Integration of Letters and Speech Sounds in Dyslexic Children Scales with Individual Differences in Reading Fluency" (Year: 2014).*
Ahissar et al., "Auditory Processing Parallels Reading Abilities in Adults," Proceedings of the National Academy of Science, vol. 97, No. 12, Jun. 6, 2000 (pp. 6832-6837).
Ahissar et al., "Dyslexia and the Failure to Form a Perceptual Anchor," Nature Neuroscience, vol. 9, No. 12, Nature Publishings, Dec. 2006 (pp. 1558-1564).
Anderson et al., "Neural Timing is Linked to Speech Perception in Noise," The Journal of Neuroscience, vol. 30, No. 14, Apr. 7, 2010 (pp. 4922-4926).
Banai et al., "Reading and Subcortical Auditory Function," Cerebral Cortex, vol. 19, Nov. 2009 (pp. 2699-2707).
Benasich et al., "Plasticity in Developing Brain: Active Auditory Exposure Impacts Prelinguistic Acoustic Mapping," The Journal of Neuroscience, vol. 34, No. 40, Oct. 1, 2014 (pp. 13349-13363).
Boets, Bart, "Dyslexia: Reconciling Controversies Within an integrative Developmental Perspective," Trends in Cognitive Sciences, vol. 18, 2014 (pp. 501-503).
Boets et al., "Intact but Less Accessible Phonetic Representations in adults with Dyslexia," Science, vol. 342, Dec. 6, 2013 (pp. 1251-1254).
Caspary et al., "Inhibitory Neurotransmission, Plasticity and Aging in the Mammalian Central Auditory System," The Journal of Experimental Biology, vol. 211, 2008 (pp. 1781-1791).
Castles et al., "Is There A Causal Link from Phonological Awareness to Success in Learning to Read?" Cognition, vol. 91, 2004 (pp. 77-111).
Centanni et al., "Knockdown of the Dyslexia-Associated Gene Kiaa0319 Impairs Temporal Responses to Speech Stimuli in Rat Primary Auditory Cortex," Cerebral Cortex, vol. 24, Jul. 2014 (pp. 1753-1766).
Clark et al., "Neuroanatomical Precursors of Dyslexia Identified from Pre-Reading Through to Age 11," A Journal of Neurology: Brain, vol. 137, 2014 (pp. 3136-3141).
Cunningham et al., "Neurobiologic Responses to Speech in Noise in Children With Learning Problems: Deficits and Strategies for Improvement," Clinical Neurophysiology, vol. 112, 2001 (pp. 758-767).
Finn et al., "Disruption of Functional Networks in Dyslexia: A Whole-Brain, Data-Driven Analysis of Connectivity," Biological Psychiatry, vol. 76, No. 5, Sep. 1, 2014 (21 pages).
Foorman et al., "The Role of Instruction in Learning to Read: Preventing Reading Failure in At-Risk Children," Journal of Educational Psychology, vol. 90, No. 7, 1998 (pp. 37-55).
Franceschini et al., "A Causal Link Between Visual Spatial Attention and Reading Acquisition," Current Biology, vol. 22, May 8, 2012 (pp. 814-819).
Galaburda et al., "Evidence for Aberrant Auditory Anatomy in Developmental Dyslexia," Proceedings of the National Academy of Sciences, vol. 91, Aug. 1994 (pp. 8010-8013).
Gathercole et al., "Working Memory in Children With Reading Disabilities," Journal of Experimental Child Psychology, vol. 93, 2006 (pp. 265-281).
Goswami et al., "Amplitude Envelope Onsets and Developmental Dyslexia: A New Hypothesis," Proceedings of the National Academy of Sciences, vol. 99, No. 16, Aug. 6, 2002 (pp. 10911-10916).
Goswami, Usha, "A Temporal Sampling Framework for Developmental Dyslexia," Trends in Cognitive Sciences, vol. 15, No. 1, Jan. 2011 (pp. 3-10).
Guttorm et al., "Newborn Event-Related Potentials Predict Poorer Pre-Reading Skills in Children at Risk for Dyslexia," Journal of Learning Disabilities, vol. 43, No. 5, 2010 (pp. 391-401).
Hari et al., "Impaired Processing of Rapid Stimulus Sequences in Dyslexia," Trends in Cognitive Sciences, vol. 5, No. 12, Dec. 2001 (pp. 525-532).
Hornickel et al., "Unstable Representation of Sound: A Biological Marker of Dyslexia," The Journal of Neuroscience, vol. 33, No. 8, Feb. 20, 2013 (pp. 3500-3504).
International Searching Authority, "International Search Report and Written Opinion," issued in connection with International Patent Application No. PCT/US2016/014050, dated May 6, 2016 (14 pages).
Kim et al., "Computerized Recoginition of Alzheimer Diesease-EEG Using Genetic Algorithms and Neural Network," Future Generation Computer Systems, vol. 21, 2005 (pp. 1124-1130).
Kovelman et al., "Brain Basis of Phonological Awareness for Spoken Language in Children and its Disruption in Dyslexia," Cerebral Cortex, vol. 22, No. 4, Apr. 2012 (pp. 754-764).
Kraus et al., "Auditory Neurophysiologic Responses and Discrimination Deficits in Children With Learning Problems," Science, vol. 273, No. 5277, Aug. 16, 1996 (pp. 971-973).
Kraus et al., "Consequences of Neural Asynchrony: A Case of Auditory Neuropathy," Journal of the Association for Research in Otolaryngology, vol. 1, 2000 (pp. 33-45).
Kuhl, Patricia K., "Early Language Acquisition: Cracking the Speech Code," Nature Reviews: Neuroscience, vol. 5, Nov. 2004 (pp. 831-843).
Landerl et al., "Predictors of Developmental Dyslexia in European Orthogrpahies with Varying Complexity," Journal of Child Psychology and Psychiatry, vol. 54, No. 6, 2013 (pp. 686-694).
Lehongre et al., "Altered Low-Gamma Sampling in Auditory Cortex Accounts for the Three Main Facets of Dyslexia," Neuron, vol. 72, Dec. 22, 2011 (pp. 1080-1090).
Leppanen et al., "Infant Brain Responses Associated with Related-Related Skills Before School and at School Age," Clinical Neurophysiology, vol. 42, 2011 (pp. 35-41).
McBride-Chang et al., "Cross-Cultural Similarities in the Predictors of Reading Acquisition," Child Development, vol. 73, No. 5, Sep./Oct. 2002 (pp. 1392-1407).
Nagarajan et al., "Cortical Auditory Signal Processing in Poor Readers," Proceedings of the National Academy of Sciences, vol. 96, May 1999 (pp. 6483-6488).
Norton et al., "Rapid Automatized Naming (RAN) and Reading Fluency: Implications for Understanding and Treatment of Reading Disabilities," Annual Review of Psychology, vol. 63, 2012 (pp. 427-452).
Olulade et al., "Abnormal Visual Motion Processing is not a Cause of Dyslexia," Neuron, vol. 79, Jul. 10, 2013 (pp. 180-190).
Papadimitriou et al., "Which Specific Skill developomg During Preschool Years Predict the Reading Performance in the First and Second Grade of Primary School?" Early Child Developmental Care, 2014 (18 pages).
Pegado et al., "Timing the Impact of Literacy on Visual Processing," Proceedings of the National Academy of Sciences, Early Edition, Nov. 2014 (11 pages).
Platt et al., "Embryonic Disruption of the Candidate Dyslexia Susceptibility Gene Homolog KIAA0319-Like Results in Neuronal Migration Disorders," Neurosciences, vol. 248, 2013 (pp. 585-593).
Poeppel, David, "The Analysis of Speech in Different Temporal Integration Windows: Cerebral Lateralization as 'Asymmetric Sampling in Time,'"Speech Communication, vol. 41, Aug. 2003 (pp. 245-255).
Pugh et al., "Glutamate and Choline Levels Predict Individual Differences in Reading Ability in Emergent Readers," The Journal of Neuroscience, vol. 34, No. 11, Mar. 12, 2014 (pp. 4082-4089).
Pugh et al., "The Relationship Between Phonological and Auditory Processing and Brain Organization in Beginning Readers," Brain and Language, vol. 125, 2013 (pp. 173-183).
Raschle et al., "Altered Neuronal Response During Rapid Auditory Processing and Its Relation to Phonological Processing in Prereading Children at Familial Risk for Dyslexia," Cerebral Cortex, vol. 24, Sep. 2014 (pp. 2489-2501).

(56) References Cited

OTHER PUBLICATIONS

Raschle et al., "Functional Characteristics of Developmental Dyslexia in Left-Hemispheric Posterior Brain Regions Predate Reading Onset," Proceedings of the National Academy of Sciences, vol. 109, No. 6, Feb. 7, 2012 (pp. 2156-2161).

Raschle et al., "Structural Brain Alterations Associated with Dyslexia Predate Reading Onset," NeuroImage, vol. 57, 2011 (pp. 742-749).

Rosen, Stuart, "Temporal Information in Speech: Acoustic, Auditory and Linguistic Aspects," Philosophical Transactions of the Royal Society of London. Series B: Biological Sciences, vol. 336, 1992 (pp. 367-373).

Saygin et al., "Tracking the Roots of Reading Ability: White Matter Volume and Integrity Correlate with Phonological Awareness in Prereading and Early-Reading Kindergarten Children," The Journal of Neuroscience, vol. 33, No. 33, Aug. 14, 2013 (pp. 13251-13258).

Song et al., "Test-Retest Reliablity of the Speech-Evoked Auditory Brainstem Response," Clinical Neurophysiology, vol. 122, 2011 (pp. 346-355).

Sperling et al., "Deficits in Perceptual Noise Exclusion in Developmental Dyslexia," Nature Neuroscience, vol. 8, No. 7, Jul. 2005 (pp. 862-863).

Sprenger-Charolles et al., "Development of Phonological and Orthographic Processing in Reading Aloud, in Silent Reading, and in Spelling: A Four-Year Longtidunal Study," Journal of Experimental Child Psuchology, vol. 84, No. 3, 2003 (pp. 194-217).

Tallal, Paula, "Auditory Temporal Perception, Phonics, and Reading Disabilities in Children," Brain and Language, vol. 9, 1980 (pp. 182-198).

Torgesen et al., "Preventing Reading Failure in Young Children with Phonological Processing Disabilities: Group and Individual Responses to Instruction," Journal of Educational Psychology, vol. 91, 1999 (27 pages).

Wright et al., "Deficits in Auditory Temporal and Spectral Resolution in Language-Impaired Children," Nature, vol. 387, May 1997 (pp. 176-178).

Ziegler et al., "Speech-Perception-In-Noise Deficits in Dyslexia," Developmental Science, vol. 12, No. 5, 2009 (pp. 732-745).

\* cited by examiner

FIG. 5A
FIG. 5B
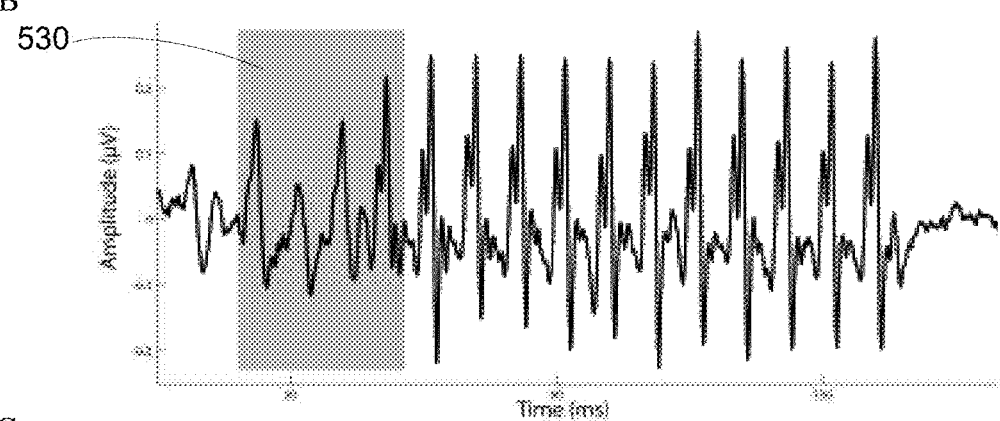
FIG. 5C
FIG. 5D
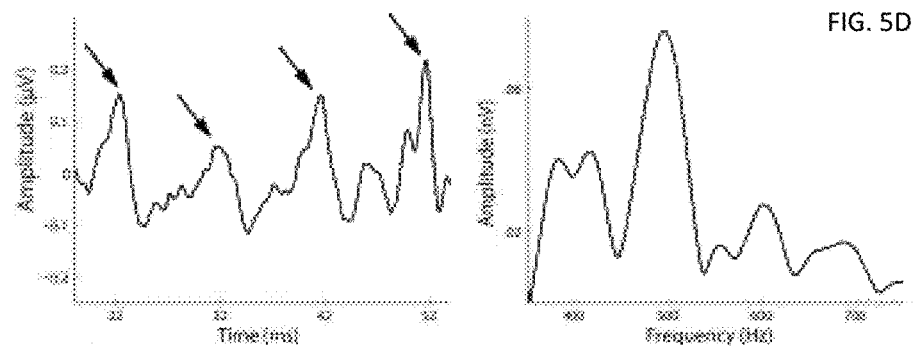
FIG. 5E
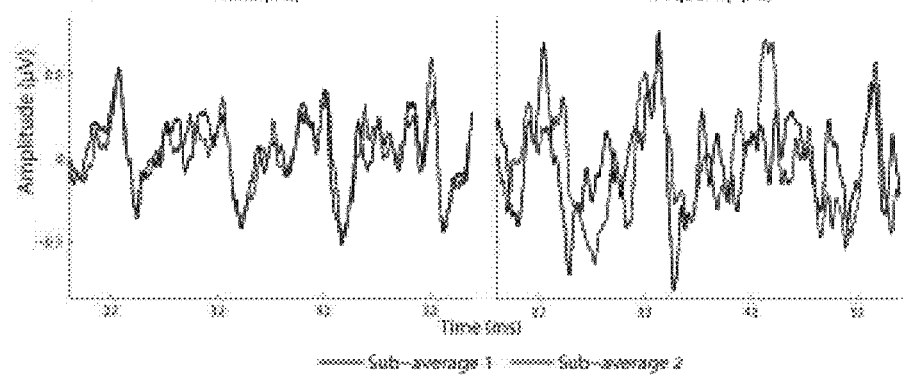

| Demographics | ΔR² | B | Neural Timing | ΔR² | β | First Formant | ΔR² | β | Neural Stability | ΔR² | β |
|---|---|---|---|---|---|---|---|---|---|---|---|
| Step 1 | 0.196~ | | Step 2A | 0.245* | | Step 2B | 0.254* | | Step 2C | 0.142* | |
| Sex | | -0.076 | Peak 21 | | 0.512** | H₃ | | 0.173 | Stability | | 0.386* |
| Age | | 0.390* | Peak 31 | | -0.242 | H₄ | | -0.409* | | | |
| Non-verbal IQ | | 0.114 | Peak 41 | | -0.054 | H₅ | | 0.251 | | | |
| | | | Peak 51 | | -0.312~ | H₆ | | 0.373* | | | |
| | | | Total R² | 0.440* | | Total R² | 0.449** | | Total R² | 0.337** | |

FIG. 13

SYSTEMS AND METHODS TO DERIVE MODELS TO EVALUATE BEHAVIOR OUTCOMES BASED ON BRAIN RESPONSES TO COMPLEX SOUNDS

CROSS-REFERENCE TO RELATED APPLICATIONS

This patent claims priority to U.S. Provisional Application Ser. No. 62/105,561, entitled "Prereading Biomarker," which was filed on Jan. 20, 2015 and is hereby incorporated herein by reference in its entirety for all purposes.

STATEMENT REGARDING FEDERALLY SPONSORED RESEARCH OR DEVELOPMENT

This invention was made with government support under grant number R01 HD069414 awarded by the National Institutes of Health. The government has certain rights in the invention.

FIELD

The presently described technology generally relates to auditory neuroscience. In particular, the presently described technology relates to systems, methods, and apparatus for generating a pre-school biomarker for literacy.

BACKGROUND

Recording the brainstem's response to sound can be used to assess integrity of a neural transmission of acoustic stimuli. Transient acoustic events induce a pattern of voltage fluctuations in the brainstem resulting in a waveform that yields information about brainstem nuclei along the central auditory pathway. Accurate stimulus timing in the auditory brainstem is a hallmark of normal perception.

Abnormal perception, understanding and processing of spoken language are fundamental criteria in the diagnosis of many learning disabilities. Currently, central auditory processing disorders are diagnosed through a central auditory processing (CAP) evaluation; speech language pathologies evaluate language disorders; and psychologists evaluate learning disorders. Audiologists and speech-language pathologists perform a series of tests, all of which are perceptual and/or audiological in nature (e.g., subjective—not physiological or objective). Auditory brainstem response (ABR) testing provides a physiological indication, but no connection has been established between conventional ABR results and learning disabilities.

Children and adults diagnosed with learning disabilities exhibit highly variable subject profiles. Many factors can contribute to current diagnosis of a learning problem. These include variations in: basic perceptual physiology, language development, cognitive function and attention, experientially developed compensatory mechanisms, exposure to previous remedial interventions and differing interpretations of diagnostic categories by clinicians. A consistent and reliable biological method for diagnosing individuals with language delay and learning disabilities, such as dyslexia, has yet to be established.

BRIEF DESCRIPTION OF SEVERAL VIEWS OF THE DRAWINGS

The following detailed description of certain embodiments will be better understood when read in conjunction with the appended drawings. For the purpose of illustrating the invention, certain embodiments are shown in the drawings. It should be understood, however, that the present invention is not limited to the arrangements and instrumentality shown in the attached drawings.

FIGS. 5($a$)-5($e$) depict an overview of an auditory-neurophysiological biomarker and three derived neural measures.

FIG. 7($b$) shows a histogram of an error of estimation between a preschooler's actual test scores and model predicted scores).

FIG. 13 shows a table of example regression results.

DETAILED DESCRIPTION OF CERTAIN EXAMPLES

Figure 1:
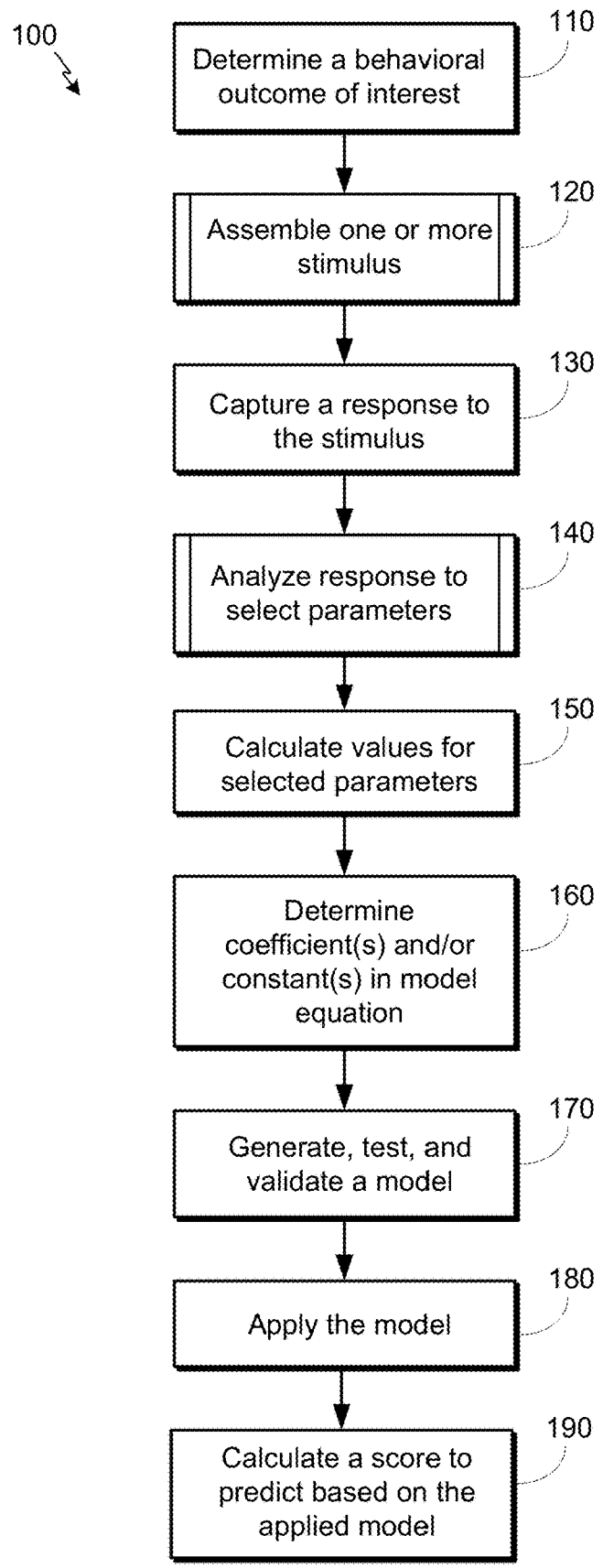
FIG. 1 illustrates a flow diagram of an example method to analyze complex auditory brainstem response (cABR) to a stimulus to generate a particular model for a behavioral outcome.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components can be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in at least one example, at least one of the elements is hereby expressly defined to include a tangible medium such as a memory, DVD, CD, Blu-ray, etc. storing the software and/or firmware.

The auditory system is an interactive system, with the auditory brainstem being the hub of this integrated network of ascending and descending projections. Electrical potentials originating in the auditory brainstem can be recorded from the human scalp with electrodes. Traditional auditory brainstem measurements have used stimuli such as clicks and tones. However, research has recently proliferated to include complex sounds such as speech, non-speech vocalization, multi-tone complexes, iterated rippled noise, environmental sounds, musical notes, and melodies, among others.

An auditory brainstem response (ABR) to complex sounds (referred to as a complex ABR or cABR) provides a wealth of information that is unavailable using a click- or tone-evoked ABR. The cABR includes a frequency following response (FFR) representing a scalp-recorded auditory evoked potential. The FFR reflects sustained neural activity over a population of neural elements, for example. The cABR also includes an onset response in addition to the FFR. Among the appeals of the cABR are (1) that it resembles incoming auditory signals, resulting in response that maintains a high fidelity to the evoking sound; (2) that responses from auditory brainstem are easily obtainable and interpretable in individuals; and (3) that as part of the interactive auditory system, the brainstem is malleable with experience and training, meaning cABR reflects these experiences.

To analyze responses to these complex sounds, cABR researchers can utilize a variety of digital signal processing techniques (DSP) beyond those needed for click- and tone-evoked ABRs. In certain examples, a suite of complex stimuli has been developed and a battery of DSP routines that support the collection and analysis of cABRs has been assembled. The stimuli in the toolbox include a variety of syllables, such as: a, da, ba, ga, ta, du, mi, spoken with three different Mandarin intonations; notes played by a cello, a tuba and a bassoon; and piano chords. The analysis routines allow for the cABR to be viewed and analyzed in the time and frequency domains in a highly flexible (e.g., user-defined) manner. Because cABRs are rich in temporal and spectral information, the use of multiple measures allows researchers to dissect individual components of the response in terms of how they reflect distinct aspects of processing and to describe the neural encoding of complex sounds in a holistic manner.

In certain examples, systems and methods are adapted to present a short auditory stimulus to a test subject. Commercially available electrophysiological acquisition technology acquires response data from the subject's brainstem response to the stimulus. Evaluation of the response data using various techniques, including statistical analysis and comparison to a database of normative results (e.g., from previously obtained and evaluated results, test scores, ranges associated with various conditions, etc.), provides an objective indication of the presence of central auditory processing disorders and related language and learning disorders.

In light of these factors and the clinical applicability of findings stemming from analysis of responses to cABR stimuli, certain examples provide systems and associated automated methods to derive statistical models, such as generalized linear models, logarithmic regression models, etc., to predict a behavior response to a cABR stimulus. Certain examples provide systems and methods of using and analyzing cABR stimulus to identify particular models of behavioral outcomes to identify and/or predict a potential problem or disability and/or to gauge progress on treatment of an issue, problem, or disability, evaluate teaching strategies, track development, etc.

Certain examples generate a formula to model a behavioral outcome or characteristic in a subject. A sound or auditory stimulus is selected to generate a response from the subject, and the response is then captured and processed to identify certain key characteristics of the stimulus sound as indicated by the captured response (e.g., transition timing, etc.). Data for the sound is analyzed to determine which cABR parameters are optimal for a statistical model (e.g., response timing (also referred to as neural timing or latency), frequency domain harmonics, stimulus-to-response and/or response-to-response correlations, frequency tracking, pitch tracking, response consistency (also referred to as neural stability), etc.), then apply statistical analysis to create the formula.

Referring to the figures, FIG. 1 illustrates a flow diagram of an example method 100 to analyze a cABR response to a stimulus to generate a particular model for a behavioral outcome. The example method 100 enables a processing and/or other computing system to predict human behavioral characteristics using models derived from electrical recordings of brain responses to complex sounds, for example.

At block 110, a behavioral outcome of interest is determined. For example, a learning disability such as a language-based reading and/or learning disability, developmental disability, developmental language delay, and/or neurologic or psychiatric condition, etc., is selected for analysis. For example, neural markers indicate reading skills in school-aged children and adults. Certain examples evaluate neural markers related to precision of information processing in noise to predict a reading disability in children before those children are old enough to start learning to read.

At block 120, one or more stimulus is assembled to elicit a response having information relevant to the desired behavioral outcome. The stimulus includes a sound having rapid changes in frequency over a short amount of time. For example, a complex sound including at least one consonant and at least one vowel to feature a transition in sound between the consonant and vowel. Additionally, a speech sound formed from the consonant-vowel combination can be superimposed and/or otherwise mixed with background noise (e.g., a plurality of voices talking together and/or other random or pseudorandom background chatter, etc.) to form a stimulus. In certain examples, a plurality of stimuli are generated for presentation to one or more subjects to elicit response(s) for analysis.

For example, the stimulus can be generated using a consonant sound combined with a longer vowel sound and mix with background noise (e.g., multiple voices talking together, etc.). For example, the subject is exposed to a /da/ sound (or a /ga/ sound, /ba/ sound, /di/ sound, /boo/ sound, or other short consonant followed by longer vowel sound, etc.) for a certain time period (e.g., 170 milliseconds (ms), etc.). In some examples, the sound (e.g., the /da/) is output in noise for the subject (e.g., a 170 ms /da/ stimulus provided via synthesizer presented against a six-person talker babble track at a +10 signal-to-noise ratio (SNR), etc.).

Alternatively or additionally, for example, time-varying speech synthesis and/or other approaches using any number of fast-moving natural or synthesized stimuli such as chirps, isolated formants, longer syllables, words, environmental sounds, etc., can be used to form a stimulus. In some such examples, the stimulus is formed from at least two sounds to create a transition (e.g., a formant transition) between each of the at least two sounds. A background sound is included with the other sounds in the stimulus which avoids the transition(s) in the formed stimulus sound (e.g., people talking, traffic sounds, other background noise, etc.).

Thus, a stimulus including a frequency sweep over time can be generated for application to a subject. Further example description of generating a stimulus can also be found in U.S. Pat. Nos. 8,014,853; 8,712,514; and 8,825,140, co-owned by the present applicant, each of which is herein incorporated by reference in its entirety.

At block 130, a response is captured based on application of the stimulus. For example, starting with the generated stimulus, a plurality of subjects (e.g., 50 subjects, 100 subjects, 200 subjects, etc.) are exposed to the stimulus and responses from the subjects can be recorded (e.g., a plurality of responses over time as the stimulus is repeated for the subjects). For example, an auditory brainstem response is recorded via one or more active electrodes placed at the ear(s), forehead, top of the head, and/or base of the skull of the subject to record to brainstem response to the cABR. Responses can be digitized, amplified, and bandpass filtered to a frequency region of interest. The responses can be processed to reject artifacts, and responses to alternating polarities can be added or subtracted and averaged. Further example description of capturing a response from a subject can also be found in U.S. Pat. Nos. 8,014,853; 8,712,514; and 8,825,140, co-owned by the present applicant, each of which is herein incorporated by reference in its entirety.

Certain examples provide characteristic waveform definition from the received response. Identifying the characteristic waveform of the brain's electrical response to the complex stimulus sound begins with the time-locked averaging of many individual subjects' response to that same stimulus. Time-locked averaging of the plurality of responses increases a signal-to-noise ratio of the characteristic waveform by amplifying common features while reducing noise and small individual differences between responses. Alternatively or in addition, an individual subject's response to a stimulus can be time-locked averaged across a large number of presentations of the same stimulus. Such processing of one or more subject responses generates a waveform that characteristically defines the brain's response to that stimulus. If a plurality of responses are time-lock averaged, the resulting waveform is an inter-subject derived response. If a single subject's response is time-locked averaged, the resulting waveform is an intra-subject average.

In certain examples, responses can be obtained and stored in a database and/or other data store for later use. Thus, for example, a system may retrieve previously generated response data and begin the process 100 at block 140 to analyze the previously captured and stored response.

At block 140, the response is analyzed to select optimal and/or other desirable cABR parameters for the determined behavioral outcome. For example, the response is analyzed to determine one or more components/parameters including neural timing, spectral features, neural stability, etc. For example, response(s) gathered from one or more subjects (e.g., 1 subject, 50 subjects, 100 subject, etc.) are analyzed to determine average and variability between individuals (e.g., on a millisecond by millisecond basis).

In certain examples, regions within a response are identified. For example, one or more regions of interest in the response are determined based on the stimulus. A brain response to sound begins with an onset peak that indicates the response to the beginning of the sound. Then, for example, if the stimulus is a consonant-vowel complex sound, the response includes three regions: a region of the response due to hearing of the consonant sound (e.g., the onset peak); a region of the response due to hearing of the vowel sound; and a region of the response due to a transition between the onset of the stimulus (e.g., consonant sound) and the vowel region (see, e.g., FIGS. 5(a)-5(e)). Similar approaches can be employed using any number of fast-moving natural or synthesized stimuli such as chirps, isolated formants, longer syllables, words, environmental sounds, etc. By recognizing characteristics of each region, the regions can be automatically identified.

The vowel region is readily identified by analyzing an end of the response to identify a series of evenly spaced peaks that are the brain's response to the fundamental frequency of the vowel sound (see, e.g., FIGS. 5(a)-5(e)). Using peak finding techniques such as a windowed, filtered, maxima and/or minima, etc., peaks can be identified and compared for consistency of temporal spacing. Additionally, this technique can be informed by a-priori knowledge about the fundamental frequency of a sound so that an expected spacing between the peaks is known. The vowel region is then defined as the temporal region between the first occurring peak in this train of peaks and the end of the response.

In some examples, the "transition" (e.g., between sounds or regions) refers to a transition of one or more formants (local spectral maxima) from one frequency to another. A vowel, on the other hand, has stable formants. Thus, in addition to identifying the evenly-spaced peaks, a formant-tracking technique, such as a linear predictive coding algorithm, establishes a time point at which the formant frequencies stabilize.

The consonant region (e.g., the region of a stimulus onset peak) can be identified using similar peak finding techniques as those used to find the vowel region. The consonant region is defined as a region between the first large peak, known as the onset peak, in the characteristic waveform, and the next peak that exceeds the onset peak's amplitude. The location of both peaks can be further informed by the a-priori knowledge of the stimulus timing and experiential knowledge of a brain's latency in response to onset of sound stimuli.

Once the consonant and vowel regions have been defined, the transition region is defined as the response in temporal period between the end of the consonant region and the beginning of the vowel region. Peaks within this region can also be identified using the same windowed peak-picking algorithm used in identifying peaks in the other two regions.

A location of the transition region can be further informed by a-priori knowledge of the structure of the stimulus. For example, a stimulus can be time-shifted re the brain response, using a technique such as cross-correlation or wavelet correlation, so that the delay after sound onset that a brain response begins can be determined (e.g., ca. 8-10 ms after sound onset). A-priori knowledge of the stimulus, such as the timepoints that define the consonant transition, can then be applied in the context of the brain response's delay to determine a region of interest.

For particular subjects, peaks can be identified within a vowel response region. Using information about the temporal location of peaks within the vowel region from the characteristic response as a template, peak searching can be seeded within the same region on individual responses to the same stimulus. By allowing the peak search to shift slightly within a range relative to the expected location, individual differences in temporal latency from the characteristic response can be captured and used for subsequent analysis. Similarly, individual differences in peak location with the transition region may be captured and used for subsequent analysis.

Thus, by analyzing the response to identify various aspects of the response (e.g., regions of the response, peaks within each region, etc.), parameters (e.g., cABR parameters) can be evaluated to build a model for determination of the behavioral outcome of interest. In certain examples, parameters can be added and/or removed and tested with respect to the developing model. If the parameter improves the model fit, the parameter can be associated with the model. If, however, the parameter worsens or otherwise fails to improve the model fit, the parameter is not associated with the model.

In certain examples, one or more databases and/or other data stores include data and results from testing of different cABR parameters on different demographics. Databases and/or data stores can also include industry-standard behavioral test results obtained from subjects of various ages for comparison in building and evaluating a model.

In determining a best fit, there are many processes by which a combination of independent variables (or features) can be derived so that combination best predicts a set of dependent variables (outcome measures) across a population of individuals. One such method is regression (e.g., general linear models such as hierarchical regression, logistic regression, ordinary least squares regression, etc.) but other methods include neural networks, latent variable modeling, support vector machines, genetic expression programming, etc. A combination of those independent variables that best predicts the values of the outcome measures can be considered a predictive model of those outcome measures (also referred to as behavioral outcomes) for a population (e.g., for individuals in that population), given a population that is appropriately-large for the chosen statistical approach. In certain examples, combinations of independent variables can be linear combinations and/or non-linear combinations. Additionally, as discussed above, some variables may provide no substantive contribution to the model and may be discarded to simplify the model's complexity. One process, known as LASSO (Least Absolute Shrinkage and Selection Operator) analysis, is a regression analysis method that performs variable selection and regularization to generate a desired model at varying degrees of complexity (e.g., with more/less independent variables contributing).

At block 150, values for the selected cABR parameters are calculated. For example, as described above, selected parameters can be calculated based on the transition region(s) between consonant and vowel sounds are determined. Further, a characteristic response for the vowel region, transition region, and consonant region can be utilized along with identification of peaks in each region using an automated peak finding method, for example. Consistent peaks can be analyzed to obtain peak-related metrics, frequency response metrics can be generated from an identification of fundamental frequencies, and consistency evaluations can be automated from the responses, for example. The combination of metrics becomes a model that predicts behavior.

In more detail, one or more features or parameters can be evaluated and utilized to generate a behavioral prediction model. For example, latency, spectral feature(s), and consistency can be evaluated with respect to a behavioral model. For latency(-ies), a difference between an expected temporal location of a peak (e.g., based on the characteristic response) and a location of that same peak in an individual's response can be used as a feature for further analysis. This difference is referred to as a peak latency, and peak latency can be computed for all peaks captured in the processes above. In turn, these peak latencies can be features of the evoked response used in model generation.

For spectral feature(s), a fast Fourier transformation (FFT) can be applied to each response in total and regionally (e.g., focusing on a particular region such as the consonant region, etc.), for example. A magnitude and frequency of a primary peak of the response/region and an area under the peak within the frequency space of the transformed data can be used as features to characterize the evoked response, as can the peaks of that peak's harmonics. These features can be used in the model generation. Additional or alternate techniques may be used to determine the spectral structure of the brain's response and relate it to the stimulus, such as wavelet cross-coherence, etc.

Neural response stability or consistency can also be used in model generation. To evaluate the trial-by-trial stability of the evoked responses, filtered, epoched, and artifact-rejected responses can be re-averaged using random selection for a number of times, n, to compute n pairs of sub-averages, for example. Each sub-average includes a percentage of the trials in a recording. Each of the pairs of sub-averages is correlated and a mean correlation coefficient (e.g., Pearson's r) calculated over a region of the response (e.g., the consonant region, etc.). The correlation coefficient can be converted to a Fisher z coefficient for statistical purposes, for example.

In addition to any features derived from the evoked response, demographic parameters, such as a subject's age, gender, etc., may be used as other features in the model. These may also be outcome measures brain responses are used to predict (for example, the presence or absence of a neurologic condition).

Further, metrics from standardized behavioral or psychological testing (e.g., intelligence quotient (IQ) scores, verbal fluency tests, reading efficiency, etc.) can be used as outcome metrics, behavioral outcomes, etc.) that the model to be generated is intended to predict. These may also be outcome measures brain responses are used to predict (for example, the presence or absence of a neurologic condition).

At block 160, coefficients and constants to be used in a model equation are determined. For example, a coefficient, weight, slope, and/or other factor associated with each of the parameters determined above can be determined to prioritize and/or otherwise weight one parameter with respect to another parameter to reduce an error of estimation in the generated model. Coefficient(s) can be determined based on selected peaks from the analyzed response data, for example. In certain examples, a best fit line through example parameter data results in a constant or y-intercept to be used in the model equation as well. In certain examples, a constant is parameterized based on a selected or otherwise specified statistical approach (e.g., in multiple regression, a constant is a y-intercept of the best fit line, etc.).

At block 170, a model is generated, tested, and validated for accuracy. Based on the selected parameters (e.g., neural timing, spectral features, and neural stability, etc.) and determined coefficient(s) and/or constants, a model of the selected behavioral outcome is generated. The model can be represented by an equation, such as a multiple regression of the selected variables (e.g., Y=a+BX, where Y is the predicted value, X is the measured parameter value, B is a rate of increase/decrease for each unit of X), and a is an intercept.

In certain examples, the model can be tested and/or validated for accuracy based on a further group of subject(s). Thus, a first group of subjects can be used to generate the model, and a second group of subjects can be used to validate the model's accuracy. For example, the second group of subjects can be exposed to the stimulus and their responses analyzed with respect to the model equation to test/validate the model's accuracy.

In some examples, the model can be validated by refitting the model n times, each time excluding 1 or more subjects from a database of subject information, and evaluating an extent to which the model fit changes. For example, the model is first fit on subjects 1-100, next fit it on subjects 1-99 to see if the fit changes, and then evaluated on subjects 1-98 and 100 to see if the fit changes, etc. If the fit is stable across all of those iterations, then the model is validated as accurate.

Another alternative and/or additional approach is to use additional behavioral/outcome tests to validate the model. For example, the model can be fit against one test of phonological awareness and validated using additional behavioral outcome measures of phonological awareness and early literacy skills.

At block 180, the model is applied to predict cognitive capability associated with the selected behavioral outcome. For example, a response to the stimulus is collected from a target (e.g., a child and/or other subject or patient). The cABR parameters associated with the model equation are calculated from the collected response. The model equation is applied using the calculated cABR parameters to calculate a score.

At block 190, the calculated score is evaluated to generate the prediction of the behavioral outcome of interest. For example, the result (the score) can be compared against a scale based on normative data. Based on the scale comparison, intervention can be triggered for the target individual. In other examples, the score is compared to a threshold or range to determine if the score fits within and/or is an outlier with respect to the threshold, range, etc., which warrants further attention, monitoring, treatment, etc.

Thus, given a model, the model can be used to predict how an individual would score on an outcome measure (e.g., reading). The individual's values for the features can be used as input for the model, and the output includes the expected (predicted) values for that individual with respect to the outcome metrics.

As described above, certain examples provide a process to build a model, which can then be applied to one or more subjects to evaluate those subject(s). The example process 100 can be repeated to build a different model to test for different conditions in subject(s). Thus, the model building process can be repeatedly executed to generate various models, and a created model can be used repeatedly to evaluate multiple subjects.

Figure 2:
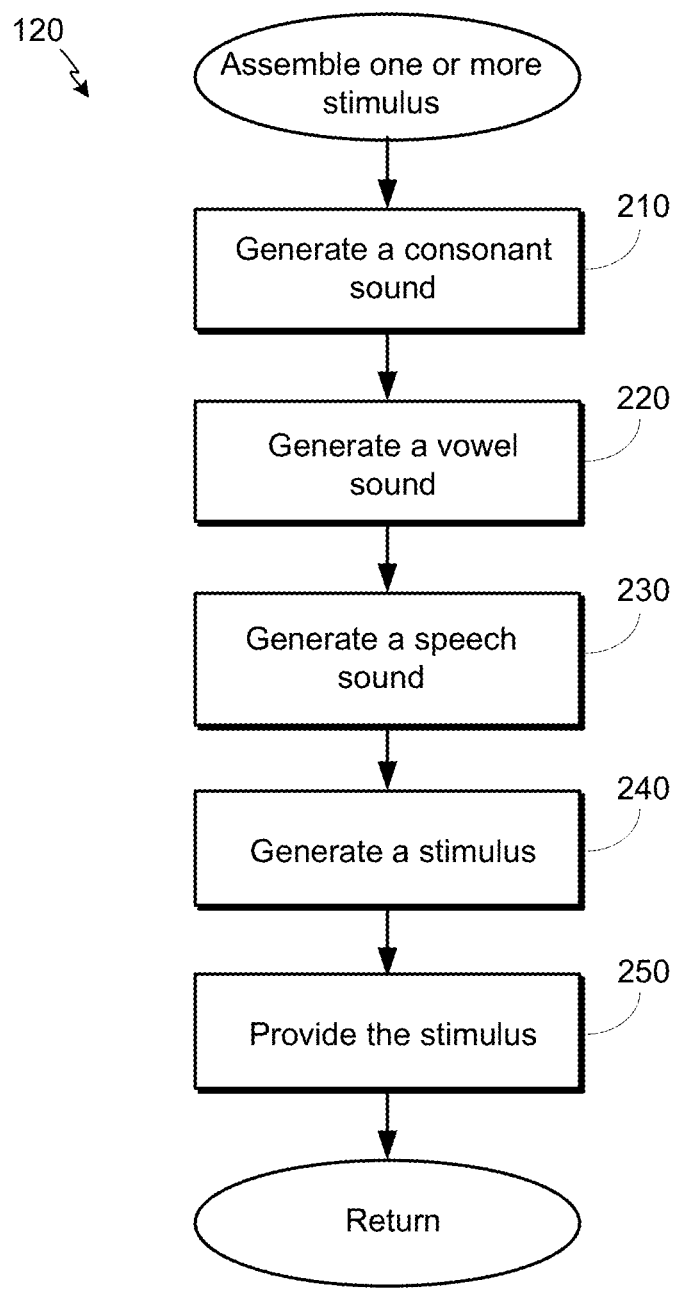
FIG. 2 illustrates a flow diagram providing further detail regarding example implementation(s) of the example method of FIG. 1 to generate a stimulus.

FIG. 2 illustrates a flow diagram providing further detail regarding example implementation(s) of block 120 of the example method 100 to generate and apply a stimulus to a subject. As described above with respect to FIG. 1, the stimulus sound can include any of a variety of real and/or synthetic sounds including a frequency sweep over time against a background (e.g., a sound including one or more transitions based on rapid changes in frequency over a period of time, a sound including a formant transition built with complementary background noise, etc.). One example of a stimulus, illustrated in the example method of FIG. 2, is a consonant-vowel combination against background noise.

At block 210, a consonant sound of a first duration is generated. For example, a /d/, /g/, /c/, etc., is selected as the consonant sound to form part of the audio stimulus to elicit a response from the subject.

At block 220, a vowel sound of a second duration is generated. In certain examples, the second duration is longer than the first duration. That is, the vowel sound is played longer in the stimulus than the consonant sound. For example, an /a/, /i/, /o/, /u/, etc., is selected as the vowel sound to accompany the /d/, /g/, /c/, etc., selected as the consonant sound to form part of the audio stimulus to elicit a response from the subject.

At block 230, a speech sound is generated by combining the consonant sound followed by the vowel sound. For example, the consonant sound and vowel sound are combined by placing the vowel sound after the consonant sound to form the speech sound to be provided in the stimulus. In other examples, the consonant sound follows the vowel sound to form the speech sound.

At block 240, the stimulus is generated by mixing a background noise with the speech sound to generate the stimulus. For example, the background noise includes a plurality of voices talking at the same time and/or approximately the same time to create a human background noise over which the stimulus can be played. In certain examples, the background noise is of a third duration which is longer than the second duration (and, therefore, also longer than the first duration).

At block 250, the stimulus is provided for output with respect to the subject. For example, the stimulus can be output as a six-formant stop consonant constructed in a synthesizer, such as a Klatt-based synthesizer at 20 kHz, etc. In certain examples, following an initial stop burst, a consonant transition (e.g., 50 ms from /d/ to /a/, etc.) during which lower formants (e.g., the lower three formants) shift in frequency (e.g., F1 400-720 Hz, F2 1700-1240 Hz, F3 2580-2500 Hz, etc.). In these examples, the lower three formants are steady for the subsequent vowel (e.g., 120 ms at /a/), and the fundamental frequency and upper three formants are steady through the stimulus (e.g., F0 100 Hz, F4 3300 Hz, F5 3750 Hz, F6 4900 Hz, etc.). The stimulus is presented against a noise or "babble" track (e.g., six voices speaking semantically anomalous English sentences at a +10 SNR, etc.). In certain examples, the babble track loops continuously since there is no phase synchrony between the onsets of the speech sound and the noise. In certain examples, the stimulus formed from the speech sound and noise is mixed into a single channel that is presented to a single ear of the subject (e.g., the right ear of the subject at 80 dB of sound pressure level (SPL) in alternating polarities through electromagnetically-shielded insert earphones, etc.). In certain examples, stimulus presentation can be controlled with a defined interstimulus interval (e.g., 61 ms, 81 ms, etc.) in a plurality of sweeps (e.g., 4200 sweeps, 6300 sweeps, etc.).

Figure 3:
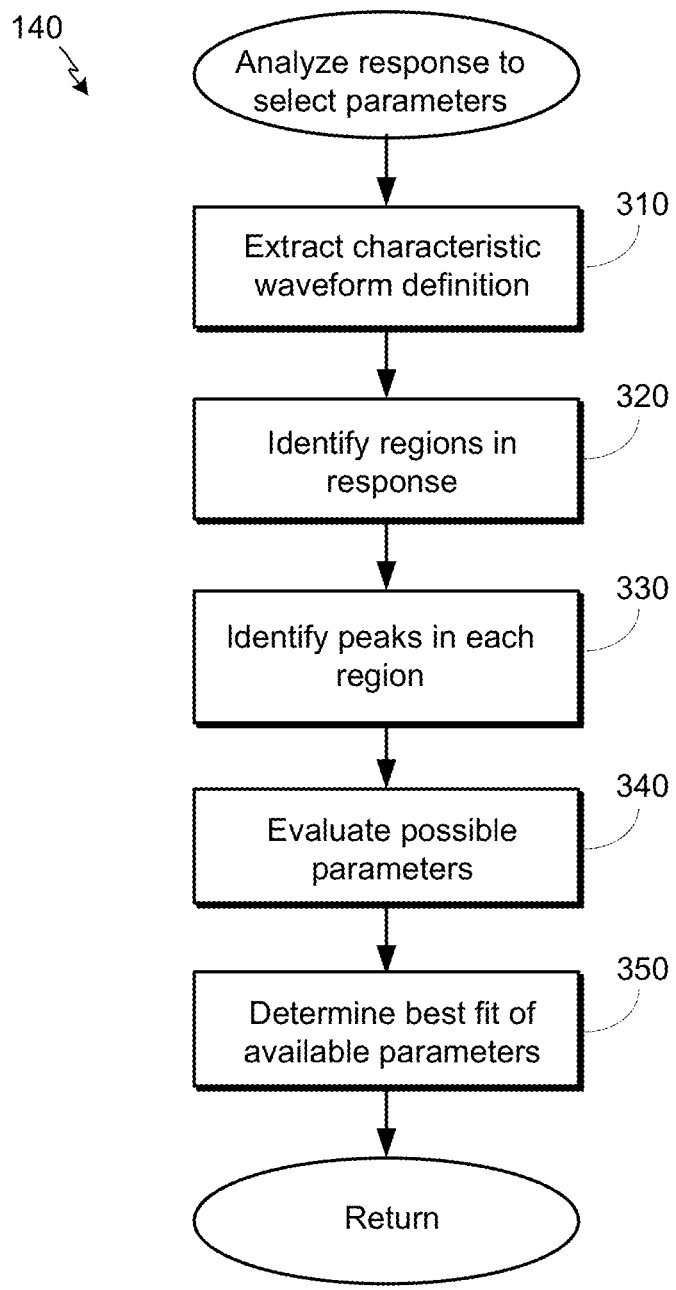
FIG. 3 illustrates a flow diagram providing further detail regarding example implementation(s) of the example method of FIG. 1 to analyze a response to a stimulus from one or more subjects.

FIG. 3 illustrates a flow diagram providing further detail regarding example implementation(s) of block 140 of the example method 100 to analyze a response to a stimulus from one or more subjects. At block 310, a characteristic waveform definition is extracted from the received response. For example, a time-locked average of one or more subject responses (e.g., inter-response and intra-response averaging)

is computed to amplify common features and reduce noise to increase signal-to-noise ratio (SNR) of the characteristic waveform.

At block 320, the characteristic waveform of the response is processed to identify distinct regions within the response. For example, a consonant-vowel complex sound includes three regions: a) a consonant sound region, b) a transition region between the consonant and the vowel, and c) a vowel sound region. These regions may be the same length and/or may be of varying lengths with respect to each other. For example, the vowel sound region may be of longer duration than the consonant sound region, and the transition region may be shorter than the consonant sound region.

The vowel region is readily identified by analyzing an end of the response to identify a series of evenly spaced peaks that are the brain's response to the fundamental frequency of the vowel sound. Using peak finding techniques such as a windowed, filtered, maxima and/or minima, etc., peaks can be identified and compared for consistency of temporal spacing. Additionally, this technique can be informed by a-priori knowledge about the fundamental frequency of a sound so that an expected spacing between the peaks is known. The vowel region is then defined as the temporal region between the first occurring peak in this train of peaks and the end of the response.

The consonant region (e.g., a region of the first onset peak for the stimulus) can be identified using similar peak finding techniques as those used to find the vowel region. The consonant region is defined as a region between the first large peak, known as the onset peak, in the characteristic waveform, and the next peak that exceeds the onset peak's amplitude. The location of both peaks can be further informed by the a-priori knowledge of the stimulus timing and experiential knowledge of a brain's latency in response to onset of sound stimuli.

Once the consonant and vowel regions have been defined, the transition region is defined as the response in temporal period between the end of the consonant region and the beginning of the vowel region. Peaks within this region can also be identified using the same windowed peak-picking algorithm used in identifying peaks in the other two regions.

At block 330, one or more peaks are identified within the determined regions of the response. For example, peaks can be identified within a vowel response region. Using information about the temporal location of peaks within the vowel region from the characteristic response as a template, peak searching can be seeded within the same region on individual responses to the same stimulus. By allowing the peak search to shift slightly within a range relative to the expected location, individual differences in temporal latency from the characteristic response can be captured and used for subsequent analysis. Similarly, individual differences in peak location with the transition region may be captured and used for subsequent analysis.

At block 340, parameters are evaluated based on the regions and determined peak information. For example, by analyzing the response to identify various aspects of the response (e.g., regions of the response, peaks within each region, etc.), parameters (e.g., cABR parameters) can be evaluated to build a model for determination of the behavioral outcome of interest. In certain examples, parameters can be added and/or removed and tested with respect to the developing model. If the parameter improves the model fit, the parameter can be associated with the model. If, however, the parameter worsens or otherwise fails to improve the model fit, the parameter is not associated with the model.

In certain examples, one or more databases and/or other data stores include data and results from testing of different cABR parameters on different demographics. Databases and/or data stores can also include industry-standard behavioral test results obtained from subjects of various ages for comparison in building and evaluating a model.

At block 350, a best fit of available parameters is determined for a desired behavioral outcome model. For example, in determining a best fit, there are many processes by which a combination of independent variables (or features) can be derived so that combination best predicts a set of dependent variables (outcome measures) across a population of individuals. One such method is regression ((e.g., general linear models such as hierarchical regression, logistic regression, ordinary least squares regression, etc.) but other methods include neural networks, latent variable modeling, support vector machines, genetic expression programming, etc. A combination of those independent variables that best predicts the values of the outcome measures can be considered a predictive model of those outcome measures (also referred to as behavioral outcomes) for a population (e.g., for individuals in that population), given a population that is appropriately-large for the chosen statistical approach. In certain examples, combinations of independent variables can be linear combinations and/or non-linear combinations. Additionally, as discussed above, some variables may provide no substantive contribution to the model and may be discarded to simplify the model's complexity. One process, known as LASSO (Least Absolute Shrinkage and Selection Operator) analysis, is a regression analysis method that performs variable selection and regularization to generate a desired model at varying degrees of complexity (e.g., with more/less independent variables contributing). Resulting selected parameters can be calculated and used to generate the desired behavioral outcome model, for example.

Figure 4:
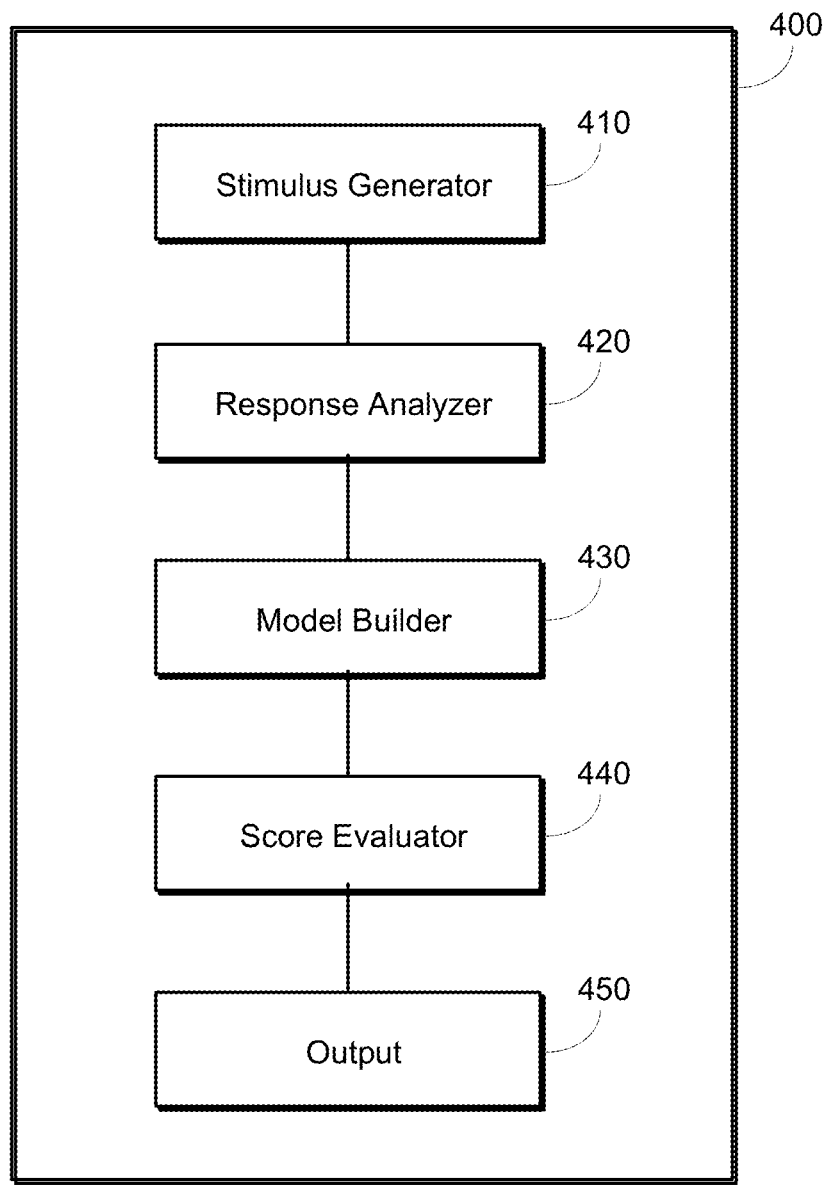
FIG. 4 illustrates a block diagram of an example system to analyze a cABR response to a stimulus to generate a behavioral outcome evaluation model.

FIG. 4 illustrates a block diagram of an example system 400 to analyze a cABR response to a stimulus to generate a behavioral outcome evaluation model. The example system 400 includes a stimulus generator 410, a response analyzer 420, a model builder 430, a score evaluator 440, and an output 450.

The example stimulus generator 410 takes a behavioral outcome of interest (e.g., a language-based reading and/or learning disability, etc.) and generates a stimulus to generate a response used to evaluate and predict that behavioral outcome. For example, one or more stimulus is assembled to elicit a response having information relevant to the desired behavioral outcome. For example, a complex sound including at least one consonant and at least one vowel to feature a transition in sound between the consonant and vowel. Additionally, a speech sound formed from the consonant-vowel combination can be superimposed and/or otherwise mixed with background noise (e.g., a plurality of voices talking together and/or other random or pseudorandom background chatter, etc.) to form a stimulus. In certain examples, a plurality of stimuli are generated for presentation to one or more subjects to elicit response(s) for analysis.

For example, the stimulus can be generated using a consonant sound combined with a longer vowel sound and mix with background noise (e.g., multiple voices talking together, etc.). For example, the subject is exposed to a /da/ sound (or a /ga/ sound, /ba/ sound, /di/ sound, /boo/ sound, or other short consonant followed by longer vowel sound, etc.) for a certain time period (e.g., 170 milliseconds (ms), etc.). In some examples, the sound (e.g., the /da/) is output in noise for the subject (e.g., a 170 ms /da/ stimulus provided via synthesizer presented against a six-person talker babble track at a +10 signal-to-noise ratio (SNR), etc.).

The example response analyzer 420 receives a response generated by applying the stimulus or stimuli to one or more subjects. For example, starting with the generated stimulus, a plurality of subjects (e.g., 50 subjects, 100 subjects, 200 subjects, etc.) are exposed to the stimulus and responses from the subjects can be recorded (e.g., a plurality of responses over time as the stimulus is repeated for the subjects). For example, an auditory brainstem response is recorded via one or more active electrodes placed at the ear(s), forehead, top of head, and/or base of the skull of the subject to record to brainstem response to the cABR. Responses can be digitized, amplified, and bandpass filtered to a frequency region of interest. The responses can be processed to reject artifacts, and responses to alternating polarities can be added and averaged.

In certain examples, the characteristic waveform of the response is processed by the response analyzer 420 to identify distinct regions within the response. For example, a consonant-vowel complex sound includes three regions: a) a consonant sound region, b) a transition region between the consonant and the vowel, and c) a vowel sound region. These regions may be the same length and/or may be of varying lengths with respect to each other. For example, the vowel sound region may be of longer duration than the consonant sound region.

The response analyzer 420 identifies a vowel region, for example, by analyzing an end of the response to identify a series of evenly spaced peaks that are the brain's response to the fundamental frequency of the vowel sound. Using peak finding techniques such as a windowed, filtered, maxima and/or minima, etc., peaks can be identified and compared for consistency of temporal spacing. Additionally, this technique can be informed by a-priori knowledge about the fundamental frequency of a sound so that an expected spacing between the peaks is known. The vowel region is then defined as the temporal region between the first occurring peak in this train of peaks and the end of the response.

The response analyzer 420 identifies a consonant region, for example, using similar peak finding techniques as those used to find the vowel region. The consonant region is defined as a region between the first large peak, known as the onset peak, in the characteristic waveform, and the next peak that exceeds the onset peak's amplitude. The location of both peaks can be further informed by the a-priori knowledge of the stimulus timing and experiential knowledge of a brain's latency in response to onset of sound stimuli.

Once the consonant and vowel regions have been defined, the response analyzer 420 defines a transition region as a temporal period between the end of the consonant region and the beginning of the vowel region. Peaks within this region can also be identified using the same windowed peak-picking algorithm used in identifying peaks in the other two regions.

The response analyzer 420 can also identify one or more peaks within the determined regions of the response. For example, peaks can be identified within a vowel response region. Using information about the temporal location of peaks within the vowel region from the characteristic response as a template, peak searching can be seeded within the same region on individual responses to the same stimulus. By allowing the peak search to shift slightly within a range relative to the expected location, individual differences in temporal latency from the characteristic response can be captured and used for subsequent analysis. Similarly, individual differences in peak location with the transition region may be captured and used for subsequent analysis.

The example model builder 430 takes results of the analyzed response from the response analyzer 420 to construct a model for evaluation, prediction, and/or other determination with respect to the behavioral outcome of interest. The model builder 430 evaluates a plurality of parameters based on the regions and determined peak information from the analyzed response, for example. For example, by analyzing the response to identify various aspects of the response (e.g., regions of the response, peaks within each region, etc.), parameters (e.g., cABR parameters) can be evaluated for the model builder 430 to build a model for determination of the behavioral outcome of interest. In certain examples, parameters can be added and/or removed and tested with respect to the developing model. If the parameter improves the model fit, the parameter can be associated with the model. If, however, the parameter worsens or otherwise fails to improve the model fit, the parameter is not associated with the model.

In certain examples, one or more databases and/or other data stores include data and results from testing of different cABR parameters on different demographics. Databases and/or data stores can also include industry-standard behavioral test results obtained from subjects of various ages for comparison in building and evaluating a model. The model builder 430 can include and/or access one or more databases and/or other data stores to evaluate potential parameters of interest for the model being built for the behavioral outcome of interest.

In more detail, the model builder 430 can evaluate and utilize one or more features or parameters to generate a behavioral prediction model. For example, latency, spectral feature(s), and consistency can be evaluated with respect to a behavioral model. For latency(-ies), a difference between an expected temporal location of a peak (e.g., based on the characteristic response) and a location of that same peak in an individual's response can be used as a feature for further analysis. This difference is referred to as a peak latency, and peak latency can be computed for all peaks captured in the processes above. In turn, these peak latencies can be features of the evoked response used in model generation.

The example model builder 430 determines a best fit of available parameters is for the behavioral outcome model. For example, in determining a best fit, there are many processes by which a combination of independent variables (or features) can be derived so that combination best predicts a set of dependent variables (outcome measures) across a population of individuals. One such method is regression ((e.g., general linear models such as hierarchical regression, logistic regression, ordinary least squares regression, etc.) but other methods include neural networks, latent variable modeling, support vector machines, genetic expression programming, etc. A combination of those independent variables that best predicts the values of the outcome measures can be considered a predictive model of those outcome measures (also referred to as behavioral outcomes) for a population (e.g., for individuals in that population), given a population that is appropriately-large for the chosen statistical approach. In certain examples, combinations of independent variables can be linear combinations and/or non-linear combinations. Additionally, as discussed above, some variables may provide no substantive contribution to the model and may be discarded to simplify the model's complexity. LASSO and/or other analyses can be applied to include and/or exclude parameters to determine the model.

In addition to any features derived from the evoked response, demographic parameters, such as a subject's age, gender, etc., may be used as other features in the model. Further, metrics from standardized behavioral or psychological testing (e.g., intelligence quotient (IQ) scores, verbal fluency tests, reading efficiency, etc.) can be used as outcome metrics that the model to be generated is intended to predict.

In certain examples, one or more coefficients and constants to be used in a model equation are also determined by the model builder 430. For example, a coefficient, weight, slope, and/or other factor associated with each of the parameters determined above can be determined to prioritize and/or otherwise weight one parameter with respect to another parameter to reduce an error of estimation in the generated model. In certain examples, a best fit line through example parameter data results in a constant or y-intercept to be used in the model equation as well.

Resulting selected parameters can be calculated and used to generate the desired behavioral outcome model, for example. In certain examples, the model is generated by the model builder 430 using a first set of response data and is then tested and/or validated using additional data sets (e.g., a first experiment to build the model and second and third experiments to test and validate the model, etc.).

Based on the evaluation, testing, and verification of a model and its parameters, a behavioral outcome model is generated by the model builder 430. In some examples, the model can be represented by an equation, such as a multiple regression of the selected variables (e.g., Y=a+BX, where Y is the predicted value, X is the measured parameter value, B is a rate of increase/decrease for each unit of X), and a is an intercept.

The example score evaluator 440 receives the model generated by the model builder 430 and applies calculated parameter values to the model to generate a score and/or other outcome indicator, predictor, etc. For example, as described above, selected parameters calculated based on the transition region(s) between consonant and vowel sounds and by peaks, latencies, consistency, etc., in and among the regions can be applied to the model equation to generate a behavior outcome score. For example, peak-related metrics, frequency response metrics, and consistency evaluations can be combined according to the model equation (e.g., a multiple regression) to generate a consonants-in-noise score indicative/predictive of a language-related learning disability in children who are not yet able to read.

For example, for spectral feature(s), a fast Fourier transformation (FFT) can be applied to each response in total and regionally (e.g., focusing on a particular region such as the consonant region, etc.), for example. A magnitude and frequency of a primary peak of the response/region and an area under the peak within the frequency space of the transformed data can be used as features to characterize the evoked response, as can the peaks of that peak's harmonics.

Additionally, neural response stability or consistency can be calculated for a response using random selection for a number of times, n, to compute n pairs of sub-averages, for example. Each sub-average includes a percentage of the trials in a recording. Each of the pairs of sub-averages is correlated and a mean correlation coefficient (e.g., Pearson's r) calculated over a region of the response (e.g., the consonant region, etc.). The correlation coefficient can be converted to a Fisher z coefficient for statistical purposes, for example.

The score evaluator 440 evaluates the calculated score to generate the prediction of the behavioral outcome of interest. For example, the result (the score) can be compared against a scale based on normative data (e.g., previously evaluated and stored in a database or other data store). In other examples, the score is compared to a threshold or range to determine if the score fits within and/or is an outlier with respect to the threshold, range, etc., which warrants further attention, monitoring, treatment, etc.

The example output 450 is generated based on the score evaluator's 440 evaluation of the calculated score. For example, based on the scale comparison, the output 450 can be provided to trigger intervention for a target individual (or group of individuals). The output 450 can be provided for storage, display, reporting, and/or transmission to another system to further monitor, process, evaluate, and/or treat the predicted/indicated behavior.

Thus, given a model, the model can be used to predict how an individual would score on an outcome measure (e.g., reading). The individual's values for the features can be used as input for the model, and the output includes the expected (predicted) values for that individual with respect to the outcome metrics.

Example Implementations

The following are examples to illustrate certain implementations of the methods and systems of FIGS. 1-4. The examples are provided for purposes of illustration only and validate the accuracy and usefulness of the present disclosure in evaluating behavioral outcomes of interest in subjects who are otherwise unable to communicate or convey such behavioral outcomes. Certain examples demonstrate that such analysis and determination would otherwise be unavailable until the subject could convey the behavior himself or herself, which point correction of that behavior could be ineffective or at the very least substantially less effective.

Learning to read is a fundamental developmental milestone, and achieving reading competency has lifelong consequences. Although literacy development proceeds smoothly for many children, a subset struggle with this learning process. The struggle creates a need to identify reliable biomarkers of a child's future literacy that could facilitate early diagnosis and access to crucial early interventions. Neural markers of reading skills have been identified in school-aged children and adults; many pertain to the precision of information processing in noise but it is unknown whether these markers are present in pre-reading children.

Certain examples identify and leverage brain-behavior relationships between integrity of neural coding of speech in noise and phonology. The brain-behavior relationships are used to form a predictive model of pre-literacy. Using the predictive model, performance on multiple pre-reading tests and performance across multiple domains of literacy can be predicted. This same neural coding predicts literacy and diagnosis of a learning disability in school-aged children. Certain examples offer new insight into biological constraints on preliteracy during early childhood and suggest that neural processing of consonants in noise is fundamental for language and reading development. Certain examples disclosed and described herein define a neurophysiological marker that can help identify children who are likely to struggle when they begin to read and do so before those children start learning to read.

Certain examples associate three aspects of auditory-neurophysiological processing with literacy: variability of neural firing, auditory system timing, and processing detailed acoustic features such as those found in consonants. This neural coding can play a pivotal role in reading and language development and may reflect the precision of neural processing in the central auditory system, which likely develops through the integrated neural coding of speech across multiple timescales, including syllabic, prosodic, and phonemic acoustic information. Although children are provided access to these sonic fundamentals in their everyday lives, these experiences often occur in adverse listening environments (e.g., in classrooms, outdoors, near wailing siblings, etc.) in which children need to tune out competing sounds to tune into speech. Indeed, noise places stringent demands on sensory processing, and individuals with language-based learning problems often have perceptual deficits in noise across modalities. Background noise limits access to redundant acoustic cues that are accessible to listeners in quiet. In principle, noise may obfuscate both the neural processing of an individual acoustic event (such as a phoneme) and the formation of consistent representations of successive events (such as words or sentences). If children with poor processing in noise grow up forced to make sense of speech in these noisy environments, they may fall behind their peers in language development.

Auditory system precision, such as the neural processing of speech in noise, is correlated to literacy; that is, struggling readers perform poorly on behavioral tests of auditory processing and have reduced auditory response fidelity and impaired neural encoding of rapid auditory stimuli compared to good readers. Therefore, these brain-behavior links likely reflect neural mechanisms underlying reading in general, as opposed to a parochial deficit in clinical populations. It remains open to debate, however, what role these neural mechanisms play developmentally with respect to reading, in part because it remains debated if auditory function is consistently implicated in reading impairment at all. Alternate accounts for the origins of reading impairment include sluggish processing in the magnocellular pathway, multimodal perceptual deficits grounded in inefficient short-term memory, and poor processing in cortical "reading networks" that lead to auditory impairments. There are likely many reasons that a child may be a poor reader, including genetic and environmental; while understanding the factors that cause reading impairment is an important goal, it is also important to predict which children will struggle when they begin to read.

Thus, certain examples facilitate early identification of children at risk for language learning problems based on a score calculated from neural coding of a combination of neural firing, auditory system timing, and processing of detailed acoustic features. These factors can be analyzed by capturing and processing a subject's neural response to a complex stimulus (e.g., including a consonant-to-vowel or vowel-to-consonant transition sound mixed with background noise, etc.) to calculate a score or indicator for evaluation and triggering of next action(s) with respect to the subject, depending upon a result of the evaluation. Such early identification may in turn facilitate access to early interventions that can prevent a life spent struggling to read, for example.

To date, auditory-neurophysiological markers of literacy have only been observed in children and adults who have received prolonged, formal instruction for reading. But the process of learning to read itself may induce changes in substrate reading skills and their neural foundations. Further compounding the problem is the challenge of predicting future literacy skills. There have been promising experiments reporting differences between groups of children (e.g., an at-risk group versus a control group, or a group of children who receive a diagnosis versus a group that does not, etc.). However, substantial overlap between groups (resulting in modest effect sizes) tends to thwart clinically-meaningful predictions in individual children. Early identification of children at risk for reading problems is crucial; interventions that are provided early enough can bring struggling pre-readers in line with their peers and offset years of reading difficulties. For example, in a prospective study of language-impaired children, prior studies have reported that literacy development proceeded smoothly in children whose oral language problems were resolved by age 5.5 year old. Accordingly, certain examples investigate early language skills, and their neural correlates, in pre-schoolers.

It has long been argued that reading skills are linked to the processing of rapid auditory information, meaning that struggling readers have particular problems with auditory temporal processing, including the perception and neural coding of dynamic speech elements. Certain examples evaluate neural processing of a consonant-vowel syllable in background noise. This processing in noise relies upon neural synchrony—that is, consistent and uniform neural population discharges. In humans, neural synchrony in response to the crucial phonemic features of speech may be measured through the frequency following response (FFR). The neural circuitry important for language development may not engage faithfully during every day listening experiences due to a breakdown in synchronous neural firing exacerbated by background noise. As a consequence of this poor online processing in noise, these children may lag their peers in language development. Previous studies in older children have established relationships between FFR properties and reading, and, therefore, provide empirical grounding for the current investigation. Certain examples also evaluate children's phonological skills because phonological processing (e.g., knowledge and manipulation of the sound structure of spoken language) is a chief pre-reading skill that is deficient in children with dyslexia. Certain examples hypothesize that background noise disrupts brain mechanisms involved in literacy development and predict that children with poor auditory-neurophysiological responses to speech in noise exhibit poorer early literacy skills than their peers.

Certain examples provide neural coding of consonants in noise to predict phonological processing. In such examples, a statistical model is constructed incorporating three aspects of the neural coding of consonants in noise: trial-by-trial stability, neural timing, and representation of spectral features that convey phonemic identity (see, e.g., FIGS. 5(a)-(e)), for example, in a cohort of 4-year-old children who had not yet learned to read (e.g., 37 children (21 female and 16 male); mean (M) age 54.41 months, standard deviation (SD) 3.56 months). The three aspects of neural coding of consonants in noise quantify different aspects of auditory processing and have been linked to reading skills in older children.

Figure 6:
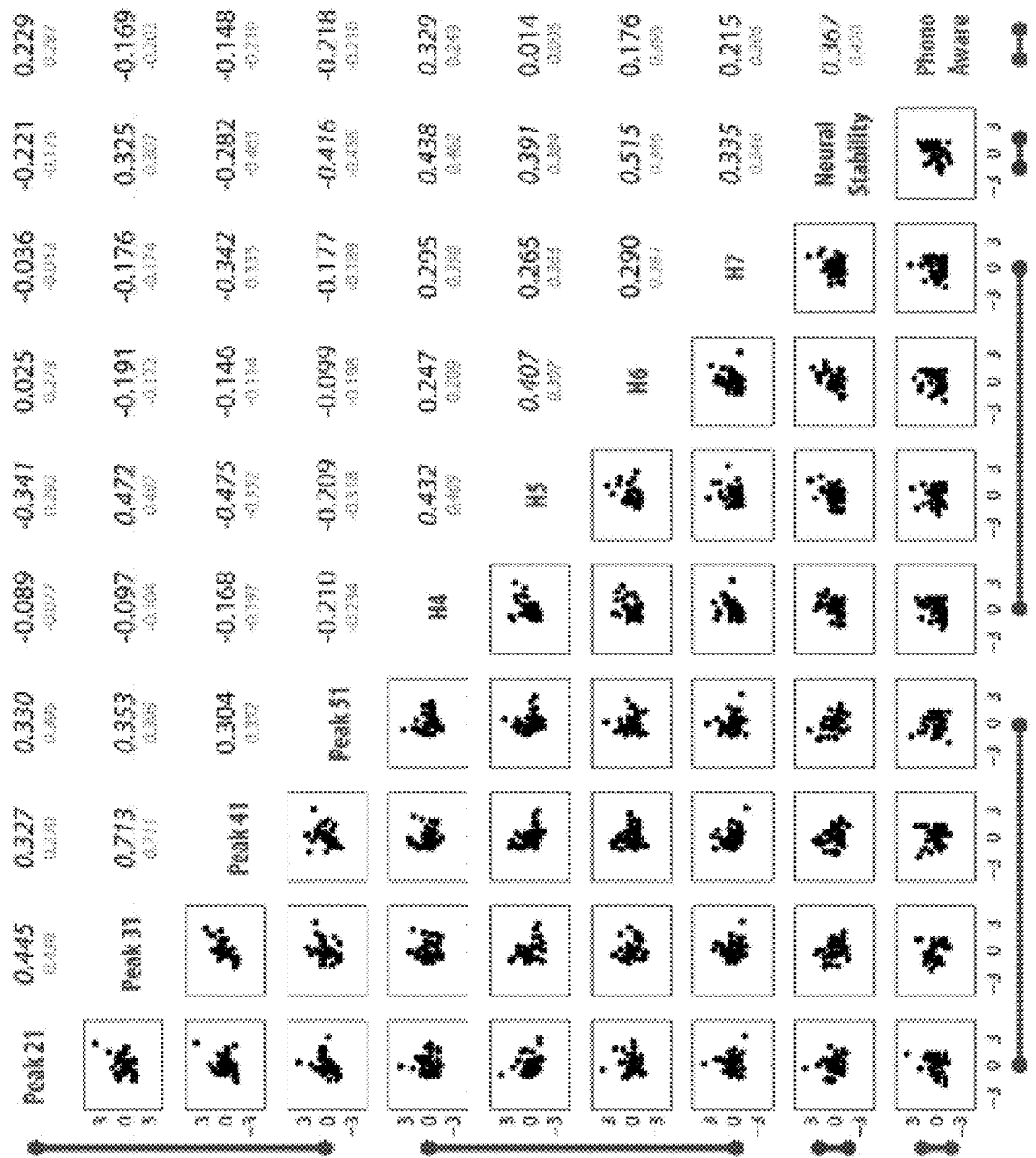
FIG. 6 depicts example correlations between neural coding measures and phonological processing.

Although these metrics (also referred to herein as features) come from a single neurophysiological recording, they are not strongly intercorrelated within an individual; thus, each metric provides unique information about the coding of different linguistic and paralinguistic parameters. For example, FIG. 6 depicts example correlations between neural coding measures and phonological processing. Neural timing measures (latencies of Peaks 21, 31, 41, and 51) are labeled in blue. Spectral measures (amplitudes at harmonics H4, H5, H6, and H7) are labeled in red. Neural stability (intertrial correlation in response to the consonant) is labeled in green, and phonological processing (e.g., CELF P-2 Phonological Awareness) is labeled in gray. Scatterplots on the lower left side of the figure shows the relations between these measures (z-transformed so that they are all on the same scale). The upper right side of the figure reports the zero-order correlation (larger font) and the partial correlation controlling for demographic factors (smaller gray font); italicized coefficients represent statistically significant correlations (e.g., p<0.05).

FIGS. 5(a)-5(e) depict an overview of an auditory-neurophysiological biomarker and three derived neural measures. As shown in FIG. 5(a), in a recording paradigm sound [da] 510, 515 is presented repeatedly over a continuous background track of nonsense sentences 520, 525 spoken by multiple talkers. As shown in the example of FIG. 5(a), a waveform 510 representing the [da] sound 515 is mixed with a second waveform 520 representing background noise (e.g., "blah", etc.) 525.

FIG. 5(b) shows a time-domain average waveform of the response to the recording paradigm sound. In comparing FIG. 5(a) and FIG. 5(b), the response of FIG. 5(b) shows many of the physical characteristics of the eliciting stimulus of FIG. 5(a). The gray box 530 shown in FIG. 5(b) highlights a time region of the response that corresponds to a consonant transition in the stimulus (e.g., the region of interest).

In FIG. 5(c), peaks of interest are identified with arrows. FIG. 5(d) shows a frequency domain representation of the grand average response to the consonant transition. In FIG. 5(e), to illustrate the trial-by-trial stability measure, two representative subjects are shown. One pair of sub-averages is shown for a first subject with high stability (left portion of FIG. 5(e)) and a second subject with poor stability (right portion of FIG. 5(e)).

In certain examples, neural coding of consonants in noise strongly predicted phonological processing in prereaders over and above demographic factors (e.g., Clinical Evaluation of Language Fundamentals (CELF) Preschool-2 (P-2) Phonological Awareness; $\Delta R^2=0.488$, $F(9,24)=4.121$, $p=0.003$; total $R^2=0.684$, $F(12,36)=4.328$, $p=0.001$; see Table 1 and FIG. 7(a); when the correlation was adjusted for test-retest variability of the behavioral test, $R^2=0.757$, where p represents a probability that a new value is different from an original value when the test is repeated or a probability that a null hypothesis is rejected; R2 is a proportion of variance explained by the model—that is, how well does the statistical model fit the data, on a scale from 0 (completely random) to 1 (perfect fit); $\Delta R2$ is the change in model fit with the addition of new parameters—how much "better" a fit for the data it is when additional parameters are added to the equation; and F is the ratio of the line of best fit of the equation when cABR parameters are added—the larger the F, the more the slope of the line (e.g., predictive power) changed (e.g., an F of 1 indicates that a slope of a regression of demographic the first part of the regression equation is equivalent to the part of the regression at which cABR parameters are added to the equation)).

Figures 7A, 7B:
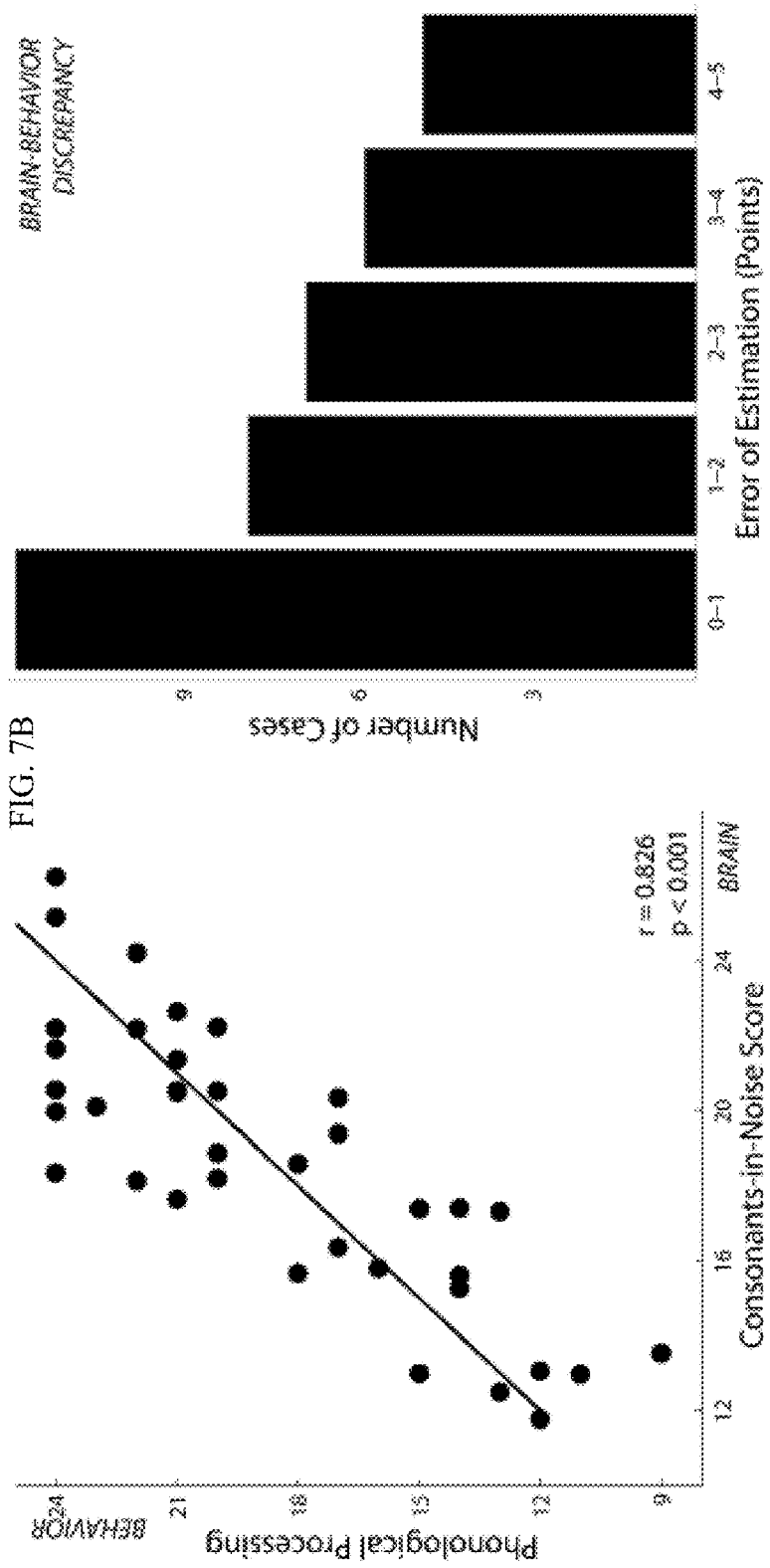
FIG. 7($a$) shows a plot illustrating a correlation between preschooler test score to model-predicted score to illustrate accuracy of the prediction.

For the majority of children, the model predicted scores within 2 points on the test, which is less than a 10% margin of error (difference between actual scores and model-predicted scores; median=1.97 points; range, 0.17-5.66 points; see FIG. 7(b)). In certain examples, results suggest that the precision and stability of coding consonants in noise parallels emergent literacy skills across a broad spectrum of competencies—all before explicit reading instruction begins.

Statistical model predictions from this regression can be used in subsequent analyses. In certain examples, model predictions reflect a "consonants-in-noise score" that may be correlated to performance cross-sectionally and longitudinally on additional behavioral tests. In examples described further below, FFRs to consonants in noise are measured, the same measures of neural coding are computed in those children, and regression parameters are applied to those children's responses. This effectively predicts performance on this test of phonological processing even though, as detailed further below, this test was not conducted in all children. In certain examples, data was not refit the data with new regression models.

Table 1 shows an example neural coding of consonants in noise as a predictor of preschooler phonological processing.

TABLE 1

| Predictor | $\Delta R^2$ | β |
|---|---|---|
| Step 1 | 0.196‡ | |
| Sex[a] | | −0.076 |
| Age | | 0.390* |
| Non-verbal IQ | | 0.114 |
| Step 2 | 0.488 | |
| Sex | | −0.162 |
| Age | | 0.452** |
| Non-verbal IQ | | 0.351* |
| Neural timing | | |
| Peak 21 | | 0.420** |
| Peak 31 | | −0.332‡ |
| Peak 41 | | −0.055 |
| Peak 51 | | −0.117 |
| First formant | | |
| $H_4$ | | 0.120 |
| $H_5$ | | −0.514** |
| $H_6$ | | 0.052 |
| $H_7$ | | 0.300* |
| Neural stability | | 0.266 |
| Total $R^2$ | 0.848‡ | |

In Table 1, a indicates sex was dummy-coded with males = 0 and females = 1,
‡indicates $p < 0.10$,
*indicates $p < 0.05$, and
**indicates $p < 0.01$.

As shown in the example of Table 1, Beta (β) represents an influence of a given parameter in the regression, standardized such that the population mean is zero and each unit is equivalent to one standard deviation.

Thus, a beta of 0.266 for neural stability indicates that each .266 standard deviations change in stability changes one unit on the dependent variable.

As shown in the example of FIG. 7(a), each monitored child's score on a phonological processing test is plotted against the model's predicted scores (e.g., n=37 for 37 children). The test score and model predicted score are highly correlated (e.g., r=0.826, p<0.001; when a correction is applied for the unreliability of the psychoeducational test, r=0.870, p<0.001, where r is a strength of the correlation indicating a similarity between two distributions (e.g., 0 indicates the two distributions are completely random, and 1 indicates the two distributions are identical). FIG. 7(b) shows a histogram of an error of estimation (e.g., a difference between a preschooler's actual and predicted scores). For a majority of monitored children, the model predicts scores within 2 points on the test.

Certain examples facilitate neural coding of consonants in noise to predict multiple preliteracy skills. Having constructed a model based on phonological processing, as described above, certain examples further explore whether model predictions generalized to multiple tests of preliteracy. The predictive model described above can be applied to twenty 3-year-olds (e.g., 9 female and 11 male; mean age 43.35 months, SD 2.50) in whom the test of phonological processing could not be administered but could conduct neurophysiological testing. The model parameters estimated above can be used and the "consonants-in-noise scores" are combined with those from the thirty-seven children from the above-described experiment. Neural coding of consonants in noise predicted performance on a test of rapid automatized naming, an additional key preliteracy skill that is thought to be highly predictive of future reading success across languages (e.g., higher predicted scores correlated with faster naming; $r(55)=-0.550$, $p<0.001$). Neural coding also predicted children's memory for spoken sentences (e.g., $r(55)=0.516$, $p<0.001$), a test that combines auditory working memory with knowledge of grammar—an additional substrate skill that contributes to literacy development and is often deficient in children with dyslexia.

In certain examples, this cohort can be divided into the two age groups. As described above, the "consonants-in-noise score" was fit to thirty-seven 4-yr olds, and the regression weights can be applied to the twenty 3-yr olds in whom phonological processing could not be measured. In the 4-yr olds, the "consonants-in-noise" score predict memory for spoken sentences (e.g., $r(35)=0.555$, $p<0.001$) and trend towards predicting faster rapid naming (e.g., $r(35)=-0.301$, $p=0.070$). In these examples, in the 3-yr olds, the model predicts rapid naming (e.g., $r(18)=-0.692$, $p=0.001$) meaning that applying the model derived above generalizes both to a new cohort and a new preliteracy skill; however, it may not predict 3-yr old's memory for spoken sentences (e.g., $r(18)=0.034$, $p=0.888$). Scatterplots for these correlations are shown in FIGS. 8(a)-(c).

Figure 8A:
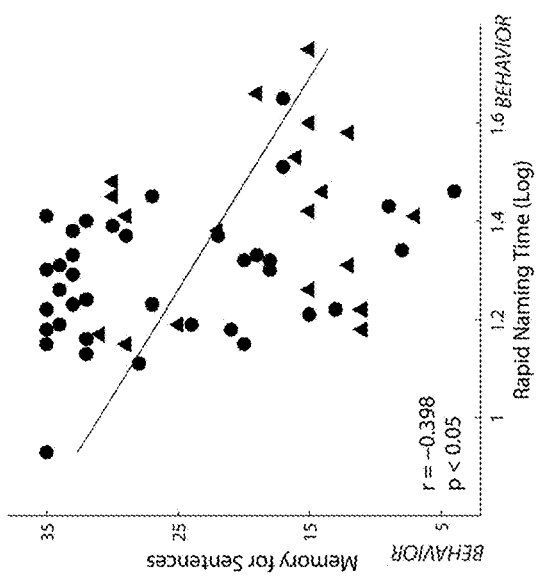
FIGS. 8($a$)-($c$) depict scatterplots showing the relations between predictions from the consonants in noise model and performance on additional tests of preliteracy, with the correlations across age groups.
Figure 8B:
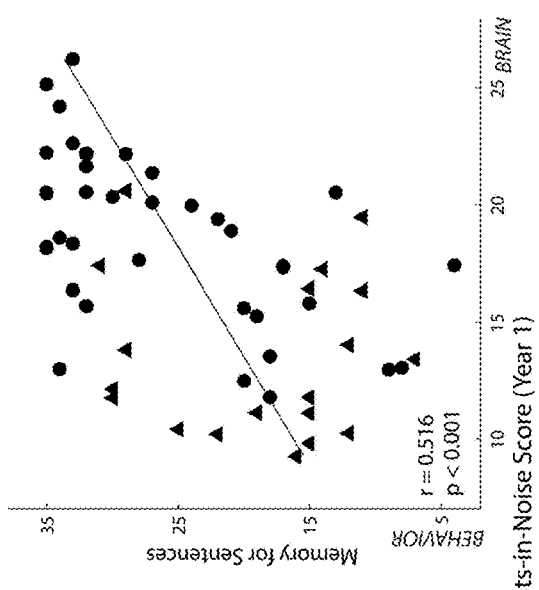
Figure 8C:
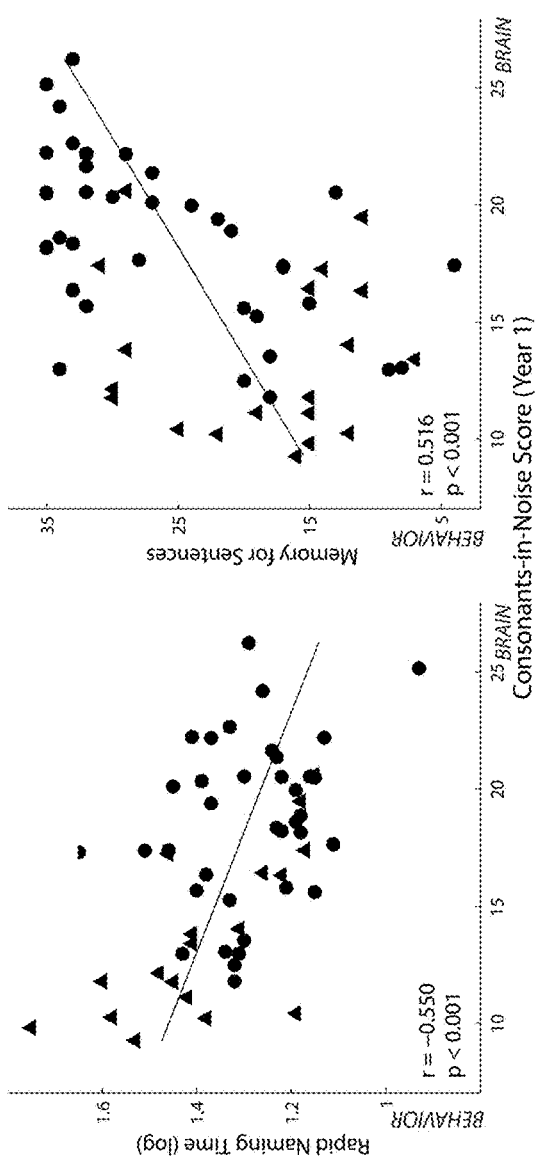

FIGS. 8(a)-(c) depict scatterplots showing the relations between predictions from the consonants in noise model and performance on additional tests of preliteracy, with the correlations across age groups. Example 4-y-olds are represented by dots and the example 3-y-olds are represented by triangles. As shown in example FIG. 8(a), neural coding of consonants in noise predicts rapid naming. FIG. 8(b) shows that neural coding of consonants in noise predicts memory for sentences. FIG. 8(c) illustrates a correlation between rapid naming and memory for sentences.

In certain examples, neural coding of consonants in noise predicts future performance on literacy tests. A subset of children tested in both examples above can returned after a certain period of time (e.g., one year later) for a behavioral test battery (N=34, 18 female). The "consonants-in-noise score" derived from the model above is taken and relations between the model's predictions and performance on a variety of literacy tests are explored after passage of time (e.g., one year) after neurophysiological assessment. The later (e.g., Year 1) neurophysiological testing predicted future performance on the same test of phonological processing—including in children too young to take this test in Year 1 (e.g., $r(32)=0.543$, $p=0.001$). These predictions generalized to future performance on a second test of phonological processing (e.g., $r(32)=0.575$, $p<0.001$) and predicted future performance on the same test of rapid automatized naming (e.g., $r(32)=-0.663$, $p<0.001$; see FIG. 9) and the same test of memory for spoken sentences (e.g., $r(32)=0.458$, $p=0.006$), for example.

Figure 9:
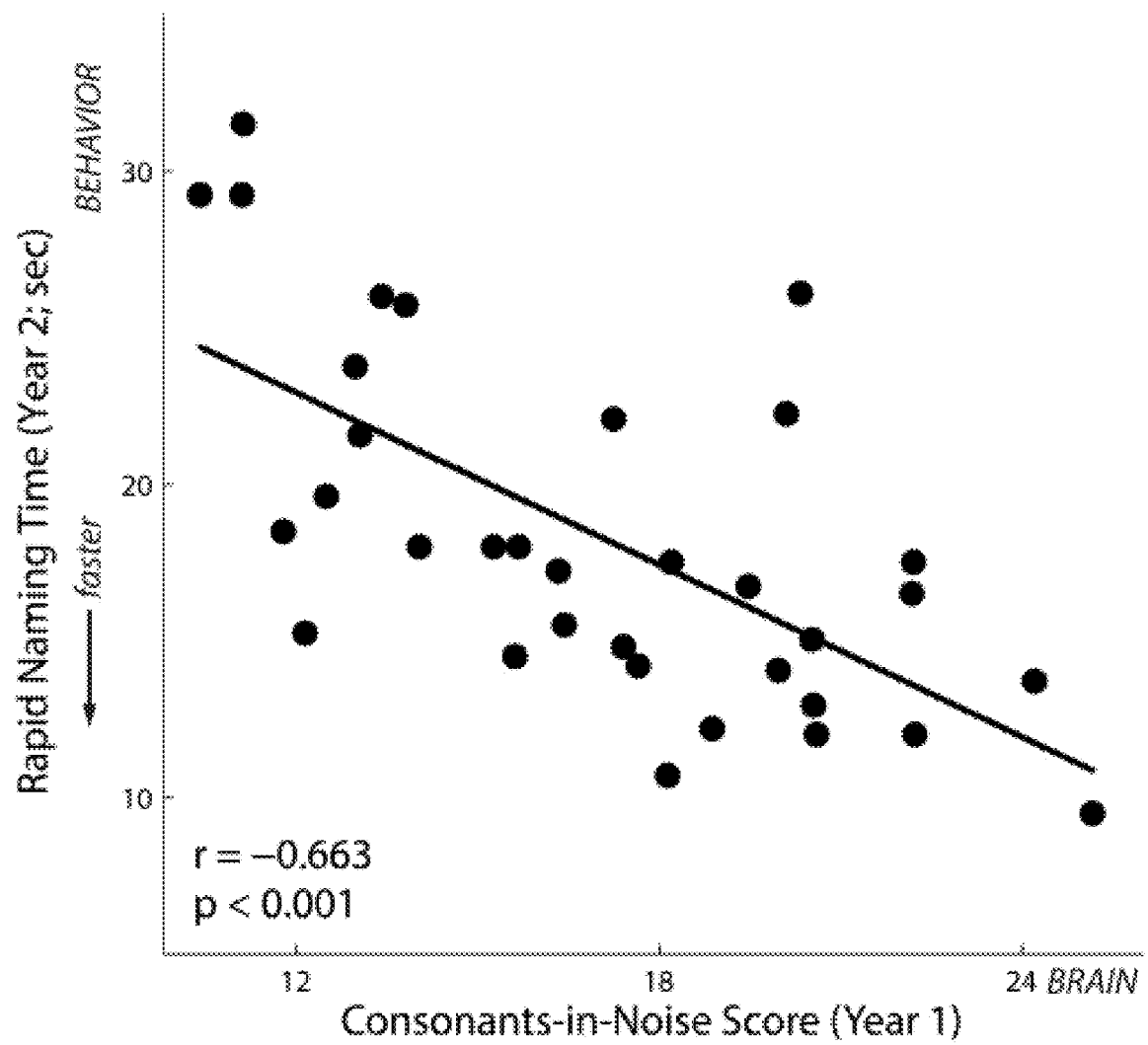
FIG. 9 depicts an example correlation between rapid naming time and consonants-in-noise score for a group of preschoolers.

FIG. 9 depicts an example correlation between rapid naming time and consonants-in-noise score for a group of preschoolers. In preschoolers (n=34), model predictions of phonological processing in Year 1 (e.g., based on neurophysiology) predict a rapid automatized naming time in Year 2, with higher predicted scores correlating with faster naming times for objects and colors (e.g., $r=-0.663$, $p<0.001$).

In certain examples, in the second year, tests can also be administered to evaluate early literacy. Neurophysiological model predictions at year one predict future performance on sight word reading (e.g., $r(32)=0.476$, $p=0.004$), spelling ($r(32)=0.415$, $p=0.015$), and a composite reading score (e.g., $r(32)=0.425$, $p=0.012$). Thus, the neural coding of consonants in noise predicts future reading achievement on standardized tests, in addition to multiple substrate skills.

Figure 10:
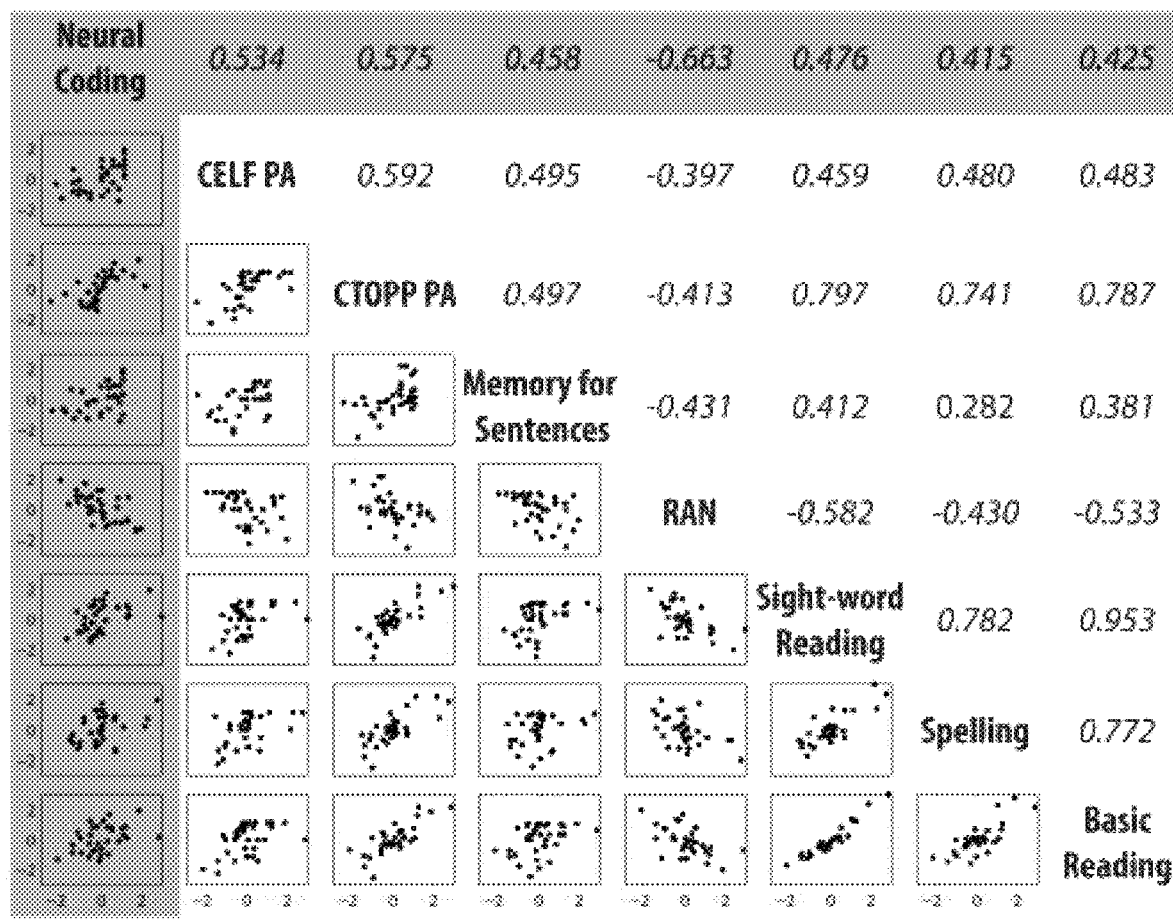
FIG. 10 shows correlations between the "consonants-in-noise" neural coding score in Year 1 and performance on tests of literacy subskills and tests of reading achievement in Year 2.

FIG. 10 shows correlations between the "consonants-in-noise" neural coding score in Year 1 (e.g., shaded in gray) and performance on tests of literacy subskills and tests of reading achievement in Year 2. Neural coding of consonants in noise predicts a range of skills, and, in the case of rapid automatized naming, for example, provides a stronger prediction of future performance than the behavioral tests of phonological processing used to derive the model. Scatterplots on the lower left side of the figure show the relations between these measures (e.g., z-transformed so that they are all on the same scale). The upper right side of the figure reports the zero-order correlation; italicized coefficients represent statistically significant correlations (e.g., $p<0.05$).

In certain examples, neural coding of consonants in noise predicts reading and diagnostic category in older children. As described above, an auditory-neurophysiological biomarker is established for pre-reading skills in preschoolers. The above-described regression model can be applied to a cohort of older children (e.g., N=55, 22 female, ages 8-14 years old, M=10.82, SD=1.7) in whom identical auditory-neurophysiological responses have been collected. Applying the regression model to the cohort of older children enables an analysis of whether the "consonants-in-noise score" derived in the 4-yr old children generalizes to a different age group, and effectively predicts how these children would have performed on the preschool tests of phonological processing, given their precision of coding consonants in noise. In school-aged children, the neural coding of consonants in noise predicted concurrent reading competence (e.g., $r(53)=0.430$, $p=0.001$) and performance on a range of literacy tests including sight word reading (e.g., $r(53)=0.408$, $p=0.002$), non-word reading (e.g., $r(53)=0.329$, $p=0.014$), spelling (e.g., $r(53)=0.327$, $p=0.015$), oral reading efficiency (e.g., $r(53)=0.319$, $p=0.018$), and phonological processing (e.g., $r(53)=0.474$, $p<0.001$).

Figure 11:
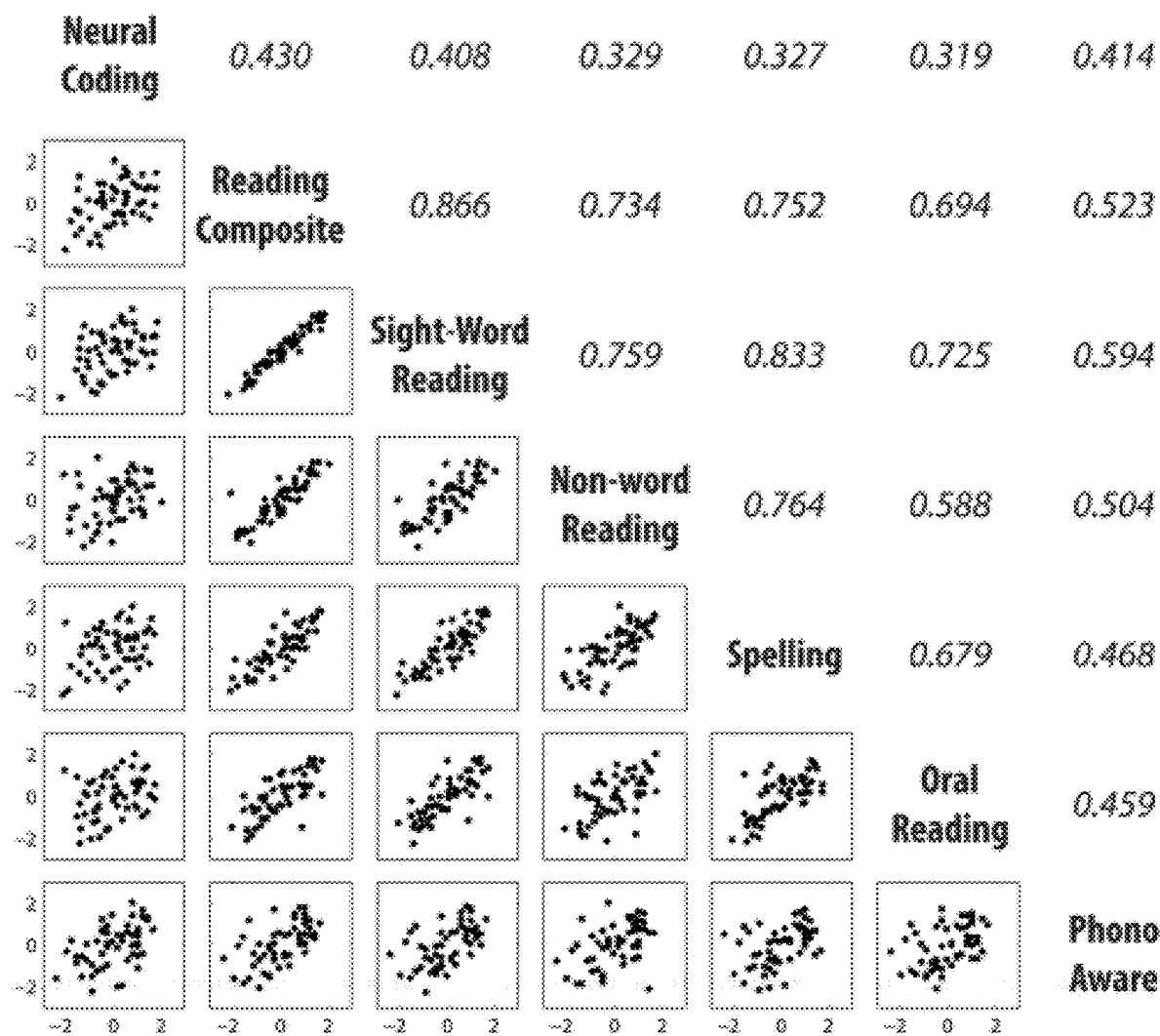
FIG. 11 shows correlations between the neural coding "consonants-in-noise" score and measures of literacy achievement in the children.

FIG. 11 shows correlations between the neural coding "consonants-in-noise" score and measures of literacy achievement in the children. The neural coding model predicts performance on a variety of literacy tests. Scatterplots on the lower left side of the figure show the relations between these measures (e.g., z-transformed so that they are all on the same scale). The upper right side of the figure reports the zero-order correlation; all correlations are statistically significant (e.g., $p<0.05$).

A subset of these children had been externally diagnosed with a learning disability (e.g., N=26); the diagnostic groups differed on their predicted scores (e.g., $F(1,53)=14.541$, $p<0.001$) and model predictions reliably classified children into diagnostic categories (e.g., discriminant function analysis: 69.1% of cases correctly classified, $\lambda=0.785$, $\chi^2=12.728$, $p<0.001$, where $\lambda$ is a proportion of variance explained by the model (e.g., 0 is completely random, 1 is perfect), and where $\chi^2=$is a "distance" from a distribution centered at zero, with an assumption that the function has no discriminant power.).

A receiver operating characteristic (ROC) analysis reveals that the model score excelled in identifying if a child was not in the reading impaired group (e.g., area under curve (AUC)=0.756; 95% confidence interval (CI), 0.627, 0.885; $p=0.001$). A ROC analysis determines an extent to which each unit increase in a given measure (e.g., a consonants in noise score, etc.) influences true positive and true negative rates of a discriminant test. From a clinical stand-point, certain examples employ the presently-disclosed consonants-in-noise approach to "clear" children as unlikely to develop an LD, thereby motivating thorough follow-up in the remaining children.

Figure 12:
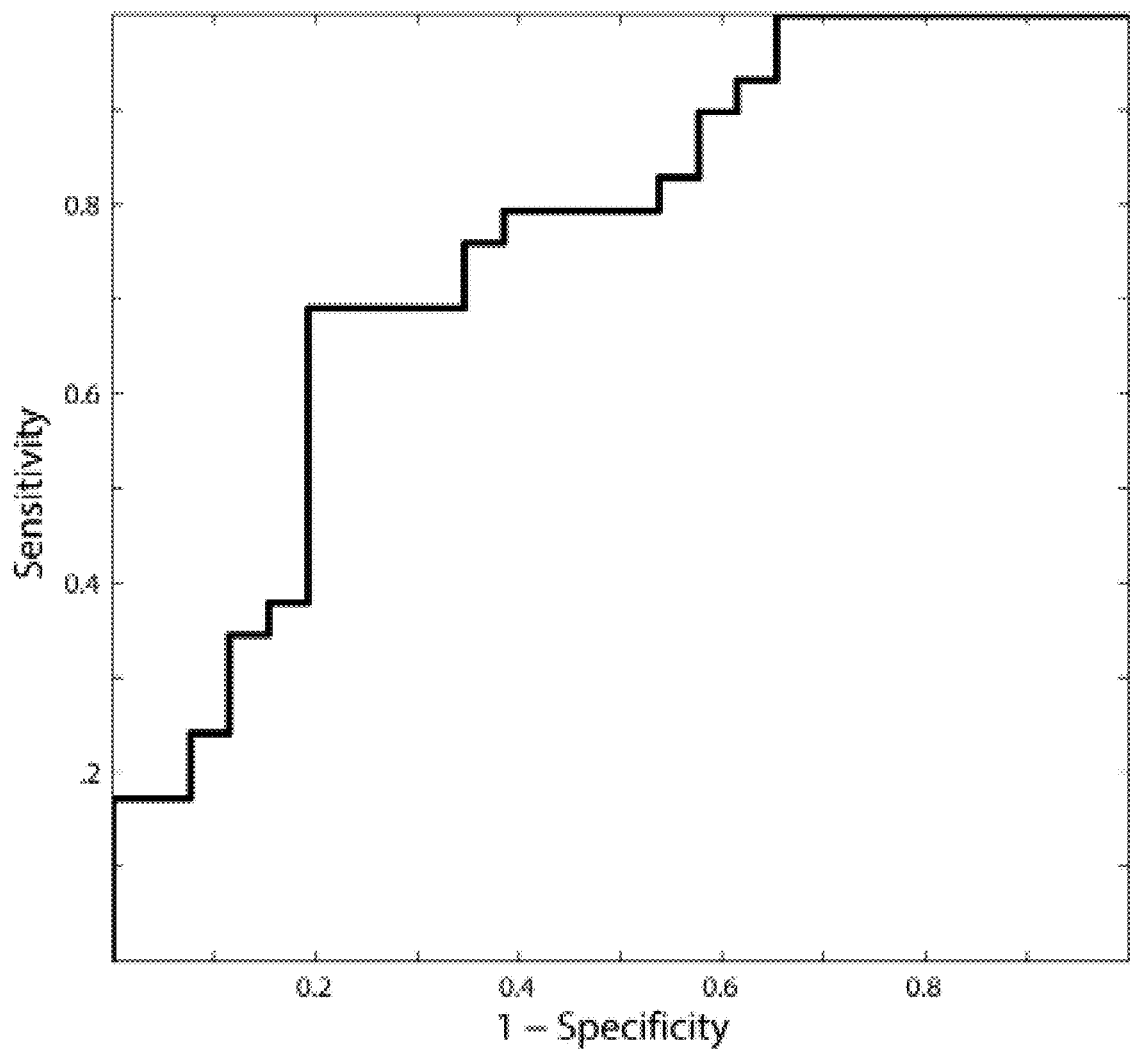
FIG. 12 illustrates an example receiver operating characteristic curve classifying children into diagnostic groups.

FIG. 12 illustrates an example ROC curve classifying children into diagnostic groups. The model is most reliable in "clearing" children as typically developing (e.g., here, sensitivity refers to a likelihood of correctly identifying a child as in the control group) rather than trending toward a learning disability.

A regression (e.g., linear regression; logistic regression; or ordinary least squares regression; all including one or more variables and/or steps) can be used to predict phonological processing from neurophysiological recordings. Demographic factors (e.g., age, sex, and non-verbal intelligence) and neurophysiological factors (e.g., neural timing, spectral features, and neural stability) can be used to form a model that estimates what percentage of variance in phonological processing is accounted for by neural coding rather than demographics. Example regression results can be provided as shown in the example table of FIG. 13.

The table of FIG. 13 shows results of modeling to generate a regression model. Neural timing (Step 2A), representation of the first formant (Step 2B), and neural stability (Step 2C) each predict phonological processing in isolation, over and above demographic factors (Step 1). As indicated in the example of FIG. 13, a indicates that "sex" is dummy-coded with males=0 and females=1, ~$p<0.10$, *$p<0.05$, **$p<0.01$.

Thus, certain examples couple physiological and phonological attributes in an age group sufficiently young to preclude confounds from prolonged and formal reading experience to identify a potential learning disability. By establishing brain-behavior links in pre-readers that are carried through to school-aged children, certain examples identify a causal, and not simply correlative, role for auditory processing in learning to read. Because the integrity of neural speech processing is linked to phonological awareness (to date, perhaps the best conventional predictor of a child's eventual reading achievement), certain examples determine neurophysiological markers to provide a biological looking glass into a child's future literacy.

Indeed, as described above, the statistical model provided herein predicts performance on reading readiness tests one year after neurophysiological assessment. Moreover, in school-aged children, such a statistical model predicts literacy and diagnostic category. Thus, in cases of learning disabilities, this prereading biomarker may represent pre-existing problems with forming sound-to-meaning and/or letter-to-sound connections that cause problems for children when they begin reading instruction, an interpretation in line with converging biological evidence. The correlations between neural coding and literacy skills were somewhat weaker in school-aged children than in pre-readers; this is consistent with the view that reading subskills mature as a function of reading experience, and that phonological processing may not play as strong a role in literacy competence for older children as it does during the early stages of reading acquisition. Moreover, older children may have developed compensatory strategies that reduce the influence of phonological processing on reading. Nevertheless, it is noteworthy that there was a consistent brain-behavior relationship observed from ages 3-14. Taken together with the breadth of relationships observed across preliteracy skills (e.g., both phonological processing and rapid naming), the neural coding of consonants in noise may reflect a child's core literacy potential.

Pharmacological studies have suggested that the neurophysiological metrics used in the statistical model rely on inhibitory neurotransmitter function; a loss of inhibitory receptors and/or an excitatory-inhibitory misbalance in auditory midbrain is linked directly to a decrease in the synchronous neural firing necessary to encode dynamic speech features such as consonants especially in adverse listening conditions. In fact, this subcortical neural synchrony is used for auditory processing in noise. Thus, the presently described biomarker may rely on the emergence of robust inhibitory function. By measuring suprathreshold responses to consonants in noise, a developing auditory brain may be taxed to reveal systematic individual differences in inhibitory processing. Individual differences in these functions may create challenges when children are trying to map sounds to meaning in noisy environments, potentially interfering with the development of range of pre-literacy skills correlated to auditory-neurophysiological responses here.

This subcortical neural synchrony emerges and is honed through a distributed, but integrated, auditory circuit. With respect to reading, auditory cortical processing is thought to bootstrap the development of fluent speech processing; eventually, children begin to associate orthographic representations with mental representations of phonemes. A breakdown in this integrative process may cause a reduction in corticofugal input in auditory midbrain (our biomarker's putative generator), especially for acoustic transients in challenging listening environments (e.g., consonants in noise). This faulty processing may be due to poor phaselocking, abnormal thalamic and cortical cytoarchitectonics, and/or sluggish attentional resources, for example. Should a child fail to learn what to pay attention to in everyday listening environments, and in turn fail to allocate appropriate attentional resources to these relevant speech cues, s/he may struggle to build robust phonemic representations. This sound-meaning disjunction may disrupt the course of auditory learning, leading to suboptimal input from descending corticocollicular fibers and cascading to a decrease in inhibitory function at the cost of synchronous firing by midbrain nuclei. In turn, without the development of refined neural coding, maladaptive compensatory mechanisms may develop that stanch the development of automaticity in reading and auditory processing in a feed-forward feed-back loop. This view is consistent with evidence that substrate reading skills (such as phonological processing) and sensory processing develop as a function of reading experience. In certain examples, midbrain function is inferred from far-field electrophysiological recordings. Nevertheless, it is intriguing to contemplate the role of inhibitory neurotransmission, and neurochemical mechanisms more broadly, with respect to language development.

Conventional tests of early literacy can be unreliable in children this young, and standardized tests of phonological processing are not available for children younger than age 4. Paradoxically, children who perform poorly on these tests have the least reliable scores because the fewest items are administered, thereby increasing potential bias from a false positive. Given the comorbidity between reading disorders and other learning disabilities, compliance with paper-and-pencil tests may be even lower in the children who stand at the highest risk for a disability and are the most important cases to screen. When these evaluations are available, they are most reliable in identifying a child at risk for a learning disability, rather than systematically predicting a child's position along a continuum of literacy achievement. The same may be said for previously-established neurophysiological predictors of a child's diagnosis. By establishing these brain-behavior links in preschool children, these findings can pave the way for auditory-neurophysiological assessment in even younger children, in addition to children who are difficult to test using conventional means.

Certain examples combine multiple measures of neural coding to see how they collectively predict preliteracy skills; although all came from the same neurophysiological recording, each provided unique information and they were only modestly intercorrelated (e.g., average r=0.318). Similarities and differences between these measures can also be evaluated. Certain examples provide evidence that in combination they predict several preliteracy skills and diagnostic category. However, reading impairment can arise for a number of reasons, which may have distinct pathophysiologies. In certain examples, these different aspects of neural coding are uniquely linked to different etiologies of reading impairment and/or substrate reading skills.

Certain examples establish a neural correlate of preliteracy that is carried through to school age, precedes explicit reading instruction, and predicts both a child's performance along a continuum of literacy and diagnostic category. Certain examples help facilitate both early diagnosis and interventions to improve literacy before a child begins explicit instruction. Efforts to promote literacy during early childhood can be tremendously effective, and these results open a new avenue of early identification to provide children access to these crucial interventions.

Figure 14:
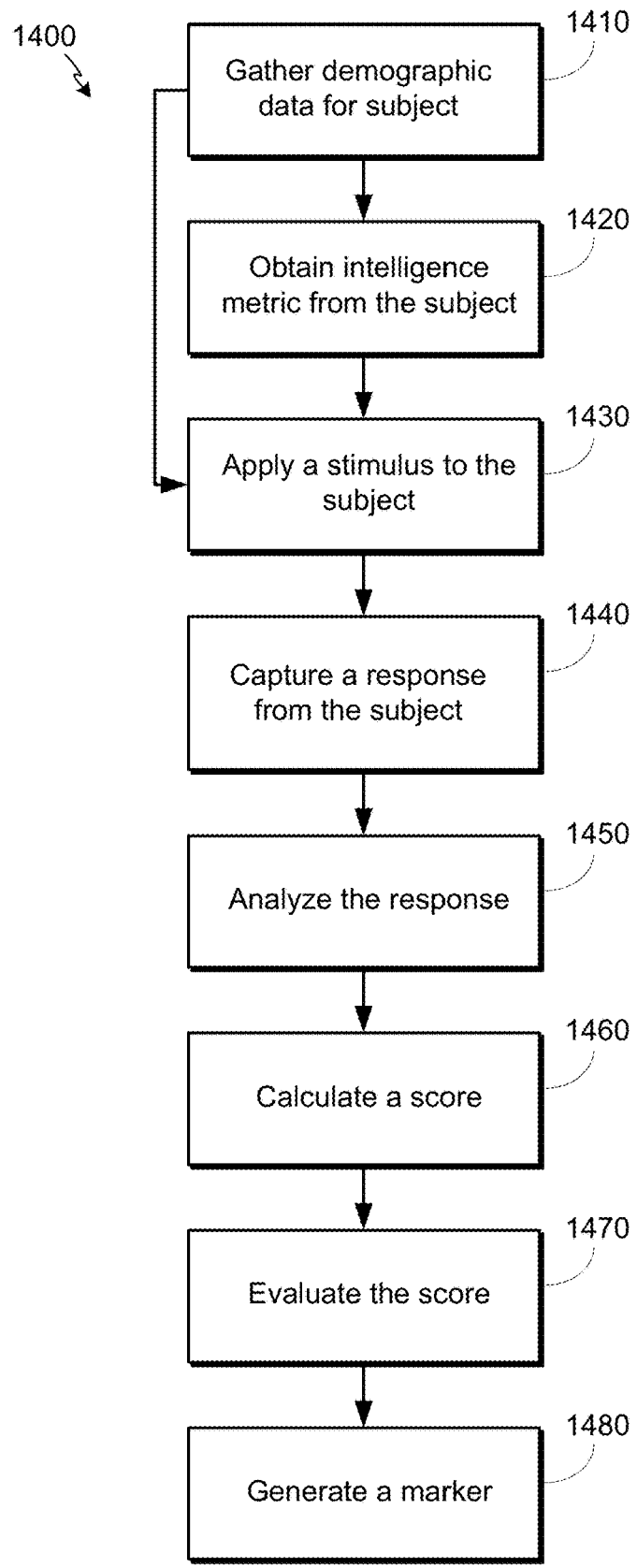
FIG. 14 illustrates a flow diagram of an example method to generate a prereading biomarker to identify a learning disability in children.

FIG. 14 illustrates a flow diagram of an example method 1400 to generate a prereading biomarker to identify a learning disability in children. At block 1410, if present and desired, demographic data may be gathered for a subject. For example, an age (e.g., reported in months, years, etc.), sex (e.g., female=0, male=1, etc.), and/or other demographic data can be obtained from a subject (e.g., one or more children, etc.).

At block 1420, if present and desired, one or more intelligence and/or behavioral metrics, such as intelligence quotient (IQ) and/or other metric, can be obtained from the subject (e.g., one or more children, etc.). For example, a non-verbal or "performance" IQ can be obtained using a test such as the Wechsler Preschool and Primary Scales of Intelligence Matrix Reasoning Test, which reports a "scaled score" on a standard psychometric scale, etc. In some examples, rather than obtaining the metric, a score can be assumed (e.g., assume that the subject scored at the 50$^{th}$ percentile). Table 2 shows an example behavioral test battery applied across a series of four experiments to develop, test, and validate a behavioral model.

TABLE 2

| Test of... | Phonological processing | Experiment | | | |
|---|---|---|---|---|---|
| | | 1 | 2 | 3 | 4 |
| CELF-P2-Phonological Awareness | Phonological processing | X | | X | |
| CELF-P2 Recalling Sentences | Auditory memory and grammar/syntax | | X | X | |
| Pre-K RAN | Rapid automatized naming | | X | X | |
| CTOPP-Phonological Awareness* | Phonological processing | | | X | X |
| WJIII-Letter Word ID | Sight word reading | | | X | X |
| WJIII-Word Attack | Non-word reading | | | | X |
| WJIII-Spelling | Spelling | | | X | X |
| TOWRE | Reading efficiency | | | | X |
| WPSSI-III | Non-verbal IQ | X | X | X | |
| WASI | Non-verbal IQ | | | | X |

*In Experiment 3 the CTOPP-2 test was used, whereas the CTOPP was used in Experiment 4.

At block 1430, a stimulus is generated and applied to the subject. As described in further detail below, the stimulus can be generated using a consonant sound combined with a longer vowel sound and mix with background noise (e.g., multiple voices talking together, etc.). For example, the subject is exposed to a /da/ sound (or a /ga/ sound, /di/ sound, /boo/ sound, or other short consonant followed by longer vowel sound, etc.) for a certain time period (e.g., 140 milliseconds (ms), 170 ms, etc.). In some examples, the sound (e.g., the /da/) is output in noise for the subject (e.g., a 170 ms /da/ stimulus provided via synthesizer presented against a six-person talker babble track at a +10 signal-to-noise ratio (SNR), etc.).

In more detail, the stimulus is generated by selecting a consonant sound. For example, a /d/, /g/, /c/, etc., is selected as the consonant sound to form part of the audio stimulus to elicit a response from the subject. Additionally, a vowel sound of a second duration is selected. In certain examples, the second duration is longer than the first duration. That is, the vowel sound is played longer in the stimulus than the consonant sound. For example, an /a/, /i/, /o/, /u/, etc., is selected as the vowel sound to accompany the /d/, /g/, /c/, etc., selected as the consonant sound to form part of the audio stimulus to elicit a response from the subject. A speech sound is generated by combining the consonant sound followed by the vowel sound. For example, the consonant sound and vowel sound are combined by placing the vowel sound after the consonant sound to form the speech sound to be provided in the stimulus. In other examples, the consonant sound follows the vowel sound to form the speed sound.

The stimulus is generated by mixing a background noise with the speech sound to generate the stimulus. For example, the background noise includes a plurality of voices talking at the same time and/or approximately the same time to create a human background noise over which the stimulus can be played. In certain examples, the background noise is of a third duration which is longer than the second duration (and, therefore, also longer than the first duration).

The stimulus can then be provided for output with respect to the subject. For example, the stimulus can be output as a six-formant stop consonant constructed in a synthesizer, such as a Klatt-based synthesizer at 20 kHz, etc. In certain examples, following an initial stop burst, a consonant transition (e.g., 50 ms from /d/ to /a/, etc.) during which lower formants (e.g., the lower three formants) shift in frequency (e.g., F1 400-720 Hz, F2 1700-1240 Hz, F3 2580-2500 Hz, etc.). In these examples, the lower three formants are steady for the subsequent vowel (e.g., 120 ms at /a/), and the fundamental frequency and upper three formants are steady through the stimulus (e.g., F0 100 Hz, F4 3300 Hz, F5 3750 Hz, F6 4900 Hz, etc.). The stimulus is presented against a noise or "babble" track (e.g., six voices speaking semantically anomalous English sentences at a +10 SNR, etc.). In certain examples, the babble track loops continuously since there is no phase synchrony between the onsets of the speech sound and the noise. In certain examples, the stimulus formed from the speech sound and noise is mixed into a single channel that is presented to a single ear of the subject (e.g., the right ear of the subject at 80 dB of sound pressure level (SPL) in alternating polarities through electromagnetically-shielded insert earphones, etc.). In certain examples, stimulus presentation can be controlled with a defined interstimulus interval (e.g., 61 ms, 81 ms, etc.) in a plurality of sweeps (e.g., 4200 sweeps, 6300 sweeps, etc.).

At block 1440, a response (e.g., FFR) is captured from the subject. For example, an auditory brainstem response is recorded via one or more active electrodes placed at the ear(s), forehead, and/or base of the skull of the subject to record to brainstem response to the cABR. Responses can be digitized, amplified, and bandpass filtered to a frequency region of interest. The responses can be processed to reject artifacts, and responses to alternating polarities can be added and averaged.

At block 1450, the response is analyzed. For example, the response is analyzed to determine one or more components including neural timing, spectral features, neural stability, etc., (see, e.g., Table 1). For example, neural timing can be determined from positive-going deflections in the evoked responses can be identified by computer algorithm using local maximum detection. In certain examples, each neural timing value is associated with a peak indicating a change between the consonant sound and the vowel sound in the stimulus. Peaks can be labeled according to their expected latency (e.g., also referred to as response timing, response latency, or neural timing). For example, a peak occurring in the response 21-22 ms after stimulus onset would be called "Peak 21". Peaks in the response are identified based on a change between consonant and vowel in the stimulus, such as a short consonant and longer vowel indicative of a sound combination difficult for children with learning problems to process. Peaks occurring in response to the consonant are called Peaks 21, 31, 41, and 51, for example. After the peaks are identified by the algorithm, selections can be adjusted manually using two subaverages of a given response as a guide, for example.

Additionally, to obtain spectral features (also referred to as frequency domain harmonics), peak amplitudes can be measured by converting the response to the frequency domain via a fast Fourier transform (FFT) to identify peaks at characteristic frequencies which give a speech sound its identity (e.g., formant harmonic frequencies, different for each consonant). For example, each spectral feature is associated with a peak representing a characteristic harmonic frequency of the speech sound. Amplitudes of such spectral peaks are identified (e.g., an H4 amplitude of the $4^{th}$ spectral peak for a harmonic at 400 Hz in the response to the 170 ms stimulus, an H5 amplitude of the $5^{th}$ spectral peak for a harmonic at 500 Hz in the response, an H6 amplitude of the $6^{th}$ spectral peak for a harmonic at 600 Hz in the response, an H7 amplitude of the $7^{th}$ spectral peak for a harmonic at 700 Hz in the response, etc.) to gauge a magnitude of responses to a first formant, which is a cue that contributes to phonemic identification. Spectral amplitudes across the frequency bins (e.g., four 40 Hz frequency bins at 400, 500, 600, and 700 Hz, etc.) can be averaged to provide a representation of spectral features, for example.

Further, response consistency (also referred to as neural stability) can be calculated by computing a plurality (e.g., 300, etc.) of sets of "paired" subaverages (e.g., each subaverage is a randomly selected set of 50% of the trials in that recording, and it's "pair" contains the remaining 50% of trials, etc.). The correlation is calculated between each pair, and the average of the 300 pairs is calculated, for example. Thus, a neural stability of responses to the stimulus is determined by sampling sub-averages of pairs of the plurality of responses.

At block 1460, a score (e.g., a consonants-in-noise score) is calculated based on the analyzed response. For example, one or more peak and amplitude values can be used in a multiple regression to calculate the score (e.g., Y=a+BX, wherein Y is the predicted value (e.g., the "consonants-in-noise score"), B is the slope (e.g., rate of increase/decrease for each unit increase in X, such as determined by statistical software based on the behavioral outcome measure and parameters/variables used to predict the behavior outcome to fit a linear model), X is the measured value on a given test, and a is the intercept (e.g., a constant in the equation), where there can be a plurality of Xs). Table 2 provides some example values to be input into the equation to compute the preliteracy measure, along with some example slopes.

TABLE 3

| Name | What it measures | B |
|---|---|---|
| a | The constant that is included in the equation (y-intercept) | 64.71170322 |
| Sex | Is the subject male or female<br>Female = 0<br>Male = 1 | −1.42467056 |
| Age | What is the subject's age<br>Reported in months (rounded) | 0.558567731 |
| Non-verbal intelligence | The non-verbal or "performance" IQ. We used the Wechsler Preschool and Primary Scales of Intelligence Matrix Reasoning Test, which reports a "scaled score" [a standard scale used in psychometrics] *Note this is not necessary. If it is missing, we can conservatively assume that the subject scored at the $50^{th}$ percentile and give them a score of 10 | 0.523178146 |
| Peak 21 | Latency of "Peak 21" in the response to the 170-ms/da/in noise (reported in ms) | 2.915113232 |
| Peak 31 | Latency of "Peak 31" in the response to the 170-ms/da/in noise (reported in ms) | −1.91211211 |
| Peak 41 | Latency of "Peak 41" in the response to the 170-ms/da/in noise (reported in ms) | −0.352504845 |
| Peak 51 | Latency of "Peak 51" in the response to the 170-ms/da/in noise (reported in ms) | −1.416818213 |
| H4 Amplitude | Amplitude of the $4^{th}$ spectral peak in response to the 170-ms/da/in noise, defined as the total amplitude from 390-410 Hz of the response converted to the frequency domain via a fast Fourier transform run over 20-60 ms with a 10 ms ramp and zero-padding (reported in μV) | 54.0468356 |

TABLE 3-continued

| Name | What it measures | B |
|---|---|---|
| H5 Amplitude | Amplitude of the 5$^{th}$ spectral peak in response to the 170-ms/da/in noise, defined as the total amplitude from 490-510 Hz of the response converted to the frequency domain via a fast Fourier transform run over 20-60 ms with a 10 ms ramp and zero-padding (reported in μV) | −290.7795279 |
| H6 Amplitude | Amplitude of the 6$^{th}$ spectral peak in response to the 170-ms/da/in noise, defined as the total amplitude from 590-610 Hz of the response converted to the frequency domain via a fast Fourier transform run over 20-60 ms with a 10 ms ramp and zero-padding (reported in μV) | 42.80802187 |
| H7 Amplitude | Amplitude of the 7$^{th}$ spectral peak in response to the 170-ms/da/in noise, defined as the total amplitude from 690-710 Hz of the response converted to the frequency domain via a fast Fourier transform run over 20-60 ms with a 10 ms ramp and zero-padding (reported in μV) | 410.2385664 |
| Response consistency | Intertrial consistency of the response to the 170-ms/da/in noise, calculated between 20-60 ms. Calculated by computing 300 sets of "paired" subaverages (each subaverage is a randomly-selected set of 50% of the trials in that recording, and its "pair" contains the remaining 50% of trails). The correlation is calculated between each pair and the average of the 300 pairs is calculated (reported as Fisher's z) | 6.378940411 |

The preliteracy measure is thus the sum of each individual's measured score multiplied by its corresponding slope (B). For example, generally, the consonants-in-noise preliteracy score Y=neural timing+spectral features+neural stability. More specifically, in the example of Table 3 above, Preliteracy Score=64.71−1.42*Sex+0.55*Age+ 0.52*Nonverbal IQ+2.91*Peak 21−1.91*Peak 31−0.35*Peak 41−1.32*Peak 51+54.05*H4− 290.78*H5+42.81*H6−410.24*H7+6.38*Response Consistency While the example provided above takes into account all elements provided in Table 2, in certain examples, one or more of these elements can be eliminated. For example, one or more of subject sex, age, non-verbal intelligence, constant, etc., can be eliminated and/or estimated in place of an actual measurement. For example, subject sex can be eliminated, and the subject can be assigned an average intelligence score of 50% in place of an actual test score obtained from the subject.

At block 1470, the calculated score is evaluated. In certain examples, the calculated score can be validated by comparison to demographic as well as neurophysiological, factors. In certain examples, independent two-step regressions can be run for each neurophysiological factor to improve model fit for a preliteracy biomarker model. In certain examples, the calculated score is compared against a scale formed based on normative data associated with literacy and/or literacy deficiency (e.g., normalize the score against an industry-standard psychological test, etc.). An evaluation of where the calculated score fits in the scale (from no problem to reading and/or other learning disability, for example) can be used to indicate whether an intervention is warranted for the subject individual.

At block 1480, a preliteracy biomarker for the subject is generated based on the evaluation of the score. For example, if an evaluation of the score based on the disability scale indicates that the subject is predicted to and/or otherwise exhibiting indication of a language-based reading disability, a preliteracy biomarker is generated to trigger further intervention with respect to the subject.

Example Processing System

Figure 15:
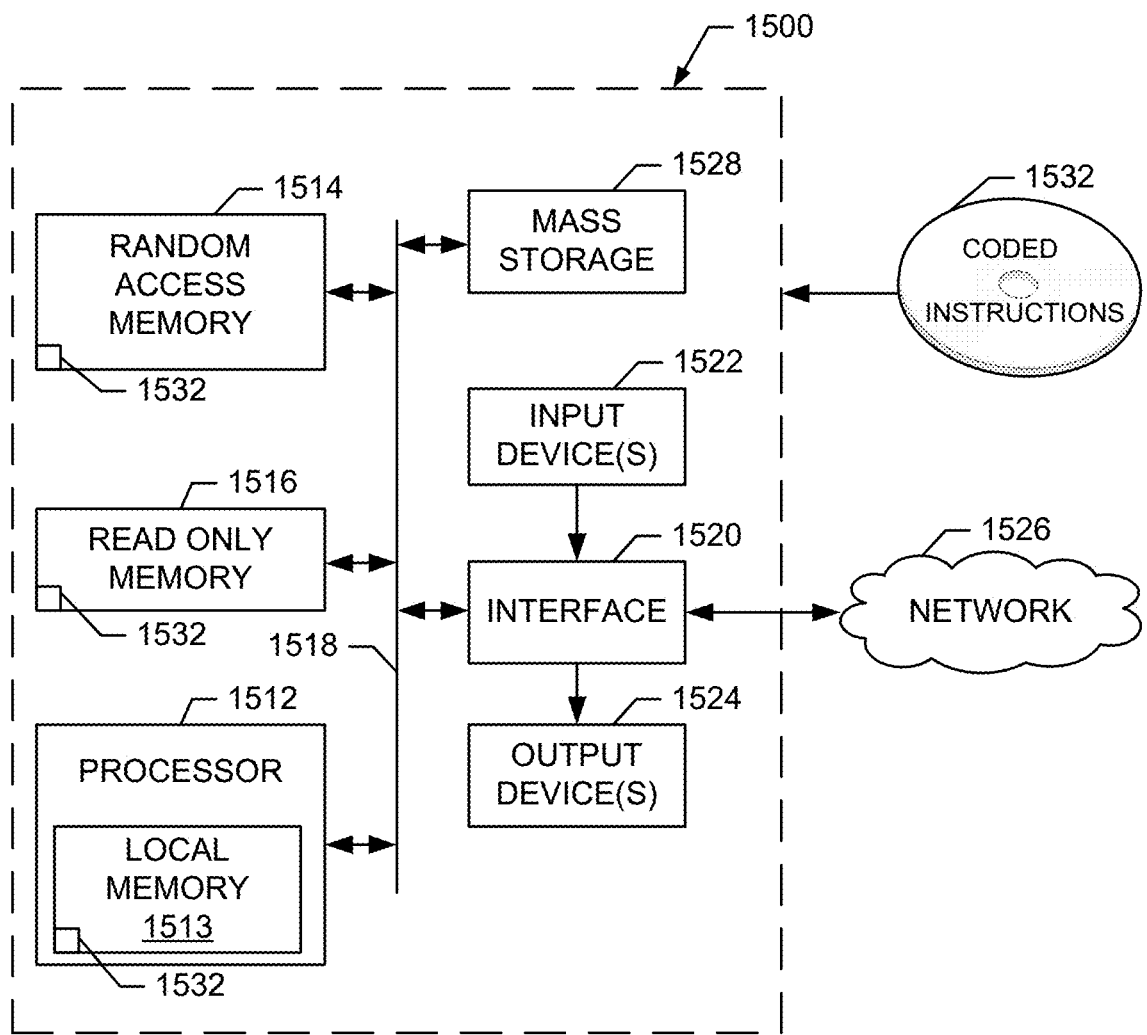
FIG. 15 is a block diagram of an example processor platform capable of executing instructions to implement the example systems, methods, views, and analysis recited herein.

FIG. 15 is a block diagram of an example processor platform 1500 capable of executing instructions to implement the example systems, methods, views, and analysis recited herein. The processor platform 1500 can be, for example, a server, a personal computer, an Internet appliance, a set top box, or any other type of computing device.

The processor platform 1500 of the instant example includes a processor 1512. For example, the processor 1512 can be implemented by one or more microprocessors or controllers from any desired family or manufacturer. The processor 1512 includes a local memory 1513 (e.g., a cache) and is in communication with a main memory including a volatile memory 1514 and a non-volatile memory 1516 via a bus 1518. The volatile memory 1514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1516 may be implemented by flash memory and/or any other desired type of memory device. Access to the main memory 1514, 1516 is controlled by a memory controller.

The processor platform 1500 also includes an interface circuit 1520. The interface circuit 1520 may be implemented by any type of interface standard, such as an Ethernet interface, a universal serial bus (USB), and/or a PCI express interface.

One or more input devices 1522 are connected to the interface circuit 1520. The input device(s) 1522 permit a user to enter data and commands into the processor 1512. The input device(s) can be implemented by, for example, a keyboard, a mouse, a touchscreen, a track-pad, a trackball, isopoint and/or a voice recognition system.

One or more output devices 1524 are also connected to the interface circuit 1520. The output devices 1524 can be implemented, for example, by display devices (e.g., a liquid crystal display, a cathode ray tube display (CRT), etc.). The interface circuit 1520, thus, typically includes a graphics driver card.

The interface circuit 1520 also includes a communication device such as a modem or network interface card to facilitate exchange of data with external computers via a network 1526 (e.g., an Ethernet connection, a digital subscriber line (DSL), a telephone line, coaxial cable, a cellular telephone system, etc.).

The processor platform 1500 also includes one or more mass storage devices 1528 for storing software and data. Examples of such mass storage devices 1528 include floppy disk drives, hard drive disks, compact disk drives and digital versatile disk (DVD) drives. The mass storage device 1528 may implement a local storage device.

Coded instructions 1532 may be stored in the mass storage device 1528, in the volatile memory 1514, in the non-volatile memory 1516, and/or on a removable storage medium such as a CD or DVD. Coded instructions 1532 can be used to implement one or more of the stimulus generator 410, response analyzer 420, model builder 430, score evaluator 440, and output 450 of the example of FIG. 4, for example.

While certain examples have been illustrated in the attached figures, one or more of the elements, processes and/or devices illustrated can be combined, divided, re-arranged, omitted, eliminated and/or implemented in other ways. The flowchart of FIG. 15 can be interpreted to include blocks representative of example machine readable instructions for implementing some or all of the systems and methods recited herein. In certain examples, machine readable instructions can include a program for execution by a processor to implement systems and methods described herein. The program can be embodied in software stored on a computer readable medium such as a CD-ROM, a floppy disk, a hard drive, a digital versatile disk (DVD), a Blu-ray disk, or a memory associated with a processor, including any other storage media in which information is stored for any duration (e.g., for extended time periods, permanently, brief instances, for temporarily buffering, and/or for caching of the information), but the entire program and/or parts thereof could alternatively be executed by a device other than the processor and/or embodied in firmware or dedicated hardware. Further, although an example program is described, many other methods of implementing the example systems and methods (and/or one or more portions of the systems and methods) can alternatively be used. For example, the order of execution of the blocks can be changed, and/or some of the blocks described can be changed, eliminated, or combined. Additionally or alternatively, some or all of a method can be performed manually.

As used herein, the term tangible computer readable medium is expressly defined to include any type of computer readable storage and to exclude propagating signals. Additionally or alternatively, the example processes can be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory or tangible computer readable medium is expressly defined to include any type of computer readable medium and to exclude propagating signals.

CONCLUSION

Thus, systems and methods disclosed and described herein generate a formula to model a behavioral outcome or characteristic in a subject. Certain examples analyze a cABR response to a stimulus to generate a particular model for a behavioral outcome. Certain examples enable a processing and/or other computing system to predict human behavioral characteristics using models derived from electrical recordings of brain responses to complex sounds.

As described above, certain examples provide systems and methods to build a model, which can then be applied to one or more subjects to evaluate those subject(s). The example systems and methods can be used to build a plurality of models to test for a plurality of conditions in subject(s). Thus, the model building process can be repeatedly executed to generate various models, and a generated model can be used repeatedly to evaluate multiple subjects.

Certain examples provide an example apparatus including a processor particularly configured to implement a response analyzer, a model builder, and a score evaluator. The example response analyzer is configured to analyze one or more response to a complex stimulus to identify a) regions in each response based on an onset peak and a transition between a consonant sound and a vowel sound and b) peaks in each region. The example model builder is configured to construct a model of a behavioral outcome based on information associated with the regions and peaks analyzed in each response, the model builder to evaluate a plurality of parameters based on the information associated with the regions and peaks to determine parameters from the plurality of parameters by applying a best fit analysis to at least one of include or exclude parameters from the plurality of parameters to determine parameters and relationship between the parameters to form the model. The example score evaluator is configured to apply the model to at least a second response from at least a first subject to generate a score by obtaining values for the parameters forming the model and combining the values according to the relationship between the parameters specified in the model, the score indicative of the behavior outcome with respect to the at least a first subject.

Certain examples provide an example computer readable medium including instructions which, when executed, particularly configure a processor to implement: a response analyzer, a model builder, and a score evaluator. The example response analyzer is configured to analyze one or more response to a complex stimulus to identify a) regions in each response based on an onset peak and a transition between a consonant sound and a vowel sound and b) peaks in each region. The example model builder is configured to construct a model of a behavioral outcome based on information associated with the regions and peaks analyzed in each response, the model builder to evaluate a plurality of parameters based on the information associated with the regions and peaks to determine parameters from the plurality of parameters by applying a best fit analysis to at least one of include or exclude parameters from the plurality of parameters to determine parameters and relationship between the parameters to form the model. The example score evaluator is configured to apply the model to at least a second response from at least a first subject to generate a score by obtaining values for the parameters forming the model and combining the values according to the relationship between the parameters specified in the model, the score indicative of the behavior outcome with respect to the at least a first subject.

Certain examples provide a method including analyzing one or more response to a complex stimulus to identify a) regions in each response based on an onset peak and a transition between a consonant sound and a vowel sound and b) peaks in each region. The example method includes constructing a model of a behavioral outcome based on information associated with the regions and peaks analyzed in each response by evaluating a plurality of parameters based on the information associated with the regions and peaks to identify parameters from the plurality of parameters; and applying a best fit analysis to at least one of include or exclude identified parameters from the plurality of parameters to determine parameters and relationship between the parameters to form the model. The example method includes facilitating application of the model to at least a second response from at least a first subject to generate a score by obtaining values for the parameters forming the model and combining the values according to the relationship between the parameters specified in the model, the score indicative of the behavior outcome with respect to the at least a first subject.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for identifying a subject in need of an intervention to improve literacy, the method comprising:
    (a) administering to a subject an acoustic stimulus a plurality of times, wherein the acoustic stimulus is comprised of a complex sound and background noise, and the complex sound comprises a consonant and a consonant-to-vowel transition;
    (b) recording, via electrodes attached to the subject, voltage potentials from the subject's brain for at least the duration of each acoustic stimulus;
    (c) analyzing the voltage potentials to determine values of one or more parameters of the brain response;
    (d) calculating a score by executing a statistical model using determined values of the one or more parameters, wherein:
        the model predicts performance on a literacy skill test using the one or more parameters of the brain response, and
        the model is generated by independently selecting the one or more parameters from a group consisting of neural timing of a response peak that is present in a time window comprising the consonant-to-vowel transition region, amplitude of a response peak that is present in a frequency domain calculated for a time window comprising the consonant-to-vowel transition region, and response consistency over a time window comprising some or all of the consonant-to-vowel transition region; and
    (e) generating an auditory-neurophysiological biomarker using the calculated score by identifying the subject as in need of an intervention when the score deviates from a control group's score or a normative score, wherein the model predicts performance on a literacy skill test significantly better than one or more demographic factors.

2. The method of claim 1, wherein the model has a receiver operating characteristic curve, wherein area under the curve is at least 0.75.

3. The method of claim 1, wherein the subject is about 6 years of age or less.

4. The method of claim 1, wherein the subject is about 5 years of age or less.

5. The method of claim 1, wherein the subject is about 4 years of age or less.

6. The method of claim 1, wherein the subject has not received explicit reading instruction.

7. The method of claim 1, wherein the subject is capable of reading.

8. The method of claim 1, wherein at least one component of the brain response comprises neural timing of a response peak that is present in a time window comprising the consonant-to-vowel transition region.

9. The method of claim 1, wherein at least one component of the brain response comprises amplitude of a peak that is present in a frequency domain calculated for a time window comprising the consonant-to-vowel transition region.

10. The method of claim 1, wherein amplitude is calculated for a peak between about 200 Hz to about 1000 Hz.

11. The method of claim 1, wherein at least one component of the brain response comprises response consistency over a time window comprising some or all of the consonant-to-vowel transition region.

12. The method of claim 1, wherein the score is a measurement produced by a statistical model that predicts performance on a literacy skill test using two or more parameters of the brain response each independently selected from the group consisting of neural timing of a response peak that is present in a time window comprising the consonant-to-vowel transition region, amplitude of a peak that is present in a frequency domain calculated for a time window comprising the consonant-to-vowel transition region, and response consistency over a time window comprising some or all of the consonant-to-vowel transition region.

13. The method of claim 1, wherein the score is a measurement produced by a statistical model that predicts performance on a literacy skill test using three or more parameters of the brain response each independently selected from the group consisting of neural timing of a response peak that is present in a time window comprising the consonant-to-vowel transition region, amplitude of a peak that is present in a frequency domain calculated for a time window comprising the consonant-to-vowel transition region, and response consistency over a time window comprising some or all of the consonant-to-vowel transition region.

14. The method of claim 1, wherein the statistical model also uses one or more demographic feature or intelligence metric.

15. The method of claim 1, wherein the consonant is a stop consonant.

16. The method of claim 1, wherein the complex sound comprises a speech syllable selected from the group consisting of /da/, /pa/, /ka/, /ta/, /ba/, and /ga/.

17. The method of claim 1, wherein the complex sound comprises a speech syllable selected from the group consisting of /da/, /pa/, /ka/, /ta/, /ba/, and /ga/, with a proviso that the complex sound is not a word.

18. The method of claim 1, wherein the complex sound consists of a speech syllable selected from the group consisting of /da/, /pa/, /ka/, /ta/, /ba/, and/ga/.

19. The method of claim 1, wherein the complex sound comprises a speech syllable /da/.

20. A method for identifying a subject at risk of performing below the 50th percentile on a literacy skill test for the subject's age group, the method comprising:
   (a) administering to a subject an acoustic stimulus a plurality of times, wherein the acoustic stimulus is comprised of a complex sound and background noise, and the complex sound comprises a consonant and a consonant-to-vowel transition;
   (b) recording, via electrodes attached to the subject, voltage potentials from the subject's brain for at least the duration of each acoustic stimulus;
   (c) analyzing the voltage potentials to determine values of one or more parameters of the brain response;
   (d) calculating a score using by executing a statistical model using one or more of the determined values of the one or more parameters, wherein:
      the model predicts performance on a literacy skill test using the one or more parameters of the brain response, and
      the model is generated by independently selecting the one or more parameters from a group consisting of neural timing of a response peak that is present in a time window comprising the consonant-to-vowel transition region, amplitude of a response peak that is present in a frequency domain calculated for a time window comprising the consonant-to-vowel transition region, and response consistency over a time window comprising some or all of the consonant-to-vowel transition region; and
   (e) generating an auditory-neurophysiological biomarker using the calculated score by identifying the subject as at risk if the score is below the 50th percentile relative to a control group's score or a normative score,
   wherein the model predicts performance on a literacy skill test significantly better than one or more demographic factors.

21. A system comprising:
   at least one electrode communicatively linked to the computing device;
   a computing device comprising at least one processor to:
      receive via the at least one electrode, voltage potentials indicative of a first brain response corresponding to an auditory pathway of a first subject, wherein the first brain response is obtained during presentation of an acoustic stimulus to the first subject, the acoustic stimulus including a complex sound comprising a consonant sound and a vowel sound;
      identify a region of the first brain response that includes an onset peak corresponding to the acoustic stimulus and a transition between the consonant sound and the vowel sound;
      based on the region, identify a response peak to identify the first subject response to the complex sound;
      generate a model based on the region and the response peak by:
         identifying a set of parameters for the model based on the region and response peak;
         applying a best fit analysis to the set of parameters to identify a first parameter and second parameter from the set of parameters for inclusion in the model; and
         generating the model based on a brain-behavior-relationship between the first parameter and the second parameter;
      automatically execute the model, using data of a second brain response corresponding to the auditory pathway of a second subject in order to calculate a score; and
      based on the execution of the model and using the calculated score, generate an indication of a behavioral outcome for the second subject when the calculated score deviates from a control group's score, a normative score, or a threshold;
   wherein the model predicts phonological processing of the second subject significantly better than one or more demographic factors.

22. The system of claim 21, wherein generating the model further comprises identifying, from the best analysis, a third parameter from the set of parameters for exclusion from the model.

23. The system of claim 21, wherein the brain-behavior-relationship represents a correlation between the set of parameters and at least one behavioral test.

24. The system of claim 21, wherein the first subject and the second subject are the same.

25. A method comprising:
   recording, via electrodes attached to a first subject, voltage potentials indicative of a first brain response corresponding to an auditory pathway of the first subject, wherein the first brain response is obtained during presentation of an acoustic stimulus to the first subject, the acoustic stimulus including a complex sound comprising a constant sound and a vowel sound;
   identifying, using a processor, a region of the first brain response that includes an onset peak corresponding to the acoustic stimulus and a transition between the consonant sound and the vowel sound;
   based on the region, identifying, using the processor, a response peak to identify the first subject response to the complex sound;
   generating, using the processor, a model based on the region and the response peak by:
      identifying a set of parameters for the model based on the region and response peak;
      applying a best fit analysis to the set of parameters to identify a first parameter and second parameter from the set of parameters for inclusion in the model; and
      generating the model based on a brain-behavior-relationship between the first parameter and the second parameter;
   automatically executing the model, using data of a second brain response corresponding to the auditory pathway of a second subject in order to calculate a score; and
   based on the execution of the model and using the calculated score, generating using the processor, an indication of a behavioral outcome for the second subject when the calculated score deviates from a control group's score, a normative score, or a threshold;
   wherein the model predicts phonological processing of the second subject significantly better than one or more demographic factors.

26. The method of claim 25, wherein generating the model further comprises identifying, from the best fit analysis, a third parameter from the set of parameters for exclusion from the model.

27. The method of claim 25, wherein the brain-behavior-relationship represents a correlation between the set of parameters and at least one behavioral test.

28. The method of claim 25, wherein the first subject and the second subject are the same.

29. A non-transitory computer-readable medium encoded with instructions for generating a model to evaluate behavioral outcomes based on brain responses, the instructions executable by a processor, comprising:

receiving, via electrodes attached to a first subject, voltage potentials indicative of a first brain response corresponding to an auditory pathway of a first subject, wherein the first brain response is obtained during presentation of an acoustic stimulus to the first subject, the acoustic stimulus including a complex sound comprising a consonant sound and a vowel sound;

identifying a region of the first brain response that includes an onset peak corresponding to the acoustic stimulus and a transition between the consonant sound and the vowel sound;

based on the region, identifying, using the processor, a response peak to identify the first subject response to the complex sound;

generating a model based on the region and the response peak by:
 identifying a set of parameters for the model based on the region and response peak;
 applying a best fit analysis to the set of parameters to identify a first parameter and second parameter from the set of parameters for inclusion in the model; and
 generating the model based on a brain-behavior-relationship between the first parameter and the second parameter;

executing the model using data of a second brain response corresponding to the auditory pathway of a second subject in order to calculate a score; and based on the execution of the model and using the calculated score, generating an indication of a behavioral outcome for the second subject when the calculated score deviates from a control group's score, a normative score, or a threshold;

wherein the model predicts phonological processing of the second subject significantly better than one or more demographic factors.

30. The non-transitory computer-readable medium of claim 29, wherein generating the model further comprises identifying, from the best fit analysis, a third parameter from the set of parameters for exclusion from the model.

31. The non-transitory computer-readable medium of claim 29, wherein the brain-behavior-relationship represents a correlation between the set of parameters and at least one behavioral test.

32. The non-transitory computer-readable medium of claim 29, wherein the first subject and the second subject are the same.

* * * * *